(12) United States Patent
McAuley et al.

(10) Patent No.: US 11,291,790 B2
(45) Date of Patent: Apr. 5, 2022

(54) BREATHING ASSISTANCE APPARATUS

(71) Applicant: Fisher & Paykel Healthcare Limited, Auckland (NZ)

(72) Inventors: Alastair Edwin McAuley, Dallas, TX (US); Oliver Gleeson, Auckland (NZ); Evan Stuart Erstich, Auckland (NZ); Simon Eric Freeman, Auckland (NZ); Neil Glen Davies, Auckland (NZ); Stephen John Schoenberg, Auckland (NZ); Kamman Law, Auckland (NZ); Craig Robert Prentice, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 16/874,532

(22) Filed: May 14, 2020

(65) Prior Publication Data

US 2020/0268998 A1 Aug. 27, 2020

Related U.S. Application Data

(63) Continuation of application No. 15/372,293, filed on Dec. 7, 2016, which is a continuation of application
(Continued)

(30) Foreign Application Priority Data

Jul. 14, 2006 (NZ) .......................................... 548575
Nov. 6, 2006 (NZ) ......................................... 551103

(51) Int. Cl.
*A61M 16/06* (2006.01)
*A61M 16/08* (2006.01)
(Continued)

(52) U.S. Cl.
CPC .... *A61M 16/0666* (2013.01); *A61M 16/0057* (2013.01); *A61M 16/024* (2017.08);
(Continued)

(58) Field of Classification Search
CPC .......... A61M 16/0605; A61M 16/0622; A61M 16/0627; A61M 16/0633; A61M 16/0683;
(Continued)

(56) References Cited

U.S. PATENT DOCUMENTS

| 301,111 A | 7/1884 | Genese |
|---|---|---|
| 472,238 A | 4/1892 | Van Orden |

(Continued)

FOREIGN PATENT DOCUMENTS

| AU | 2003246441 | 12/2003 |
|---|---|---|
| CA | 1311662 | 12/1992 |

(Continued)

OTHER PUBLICATIONS

U.S. Appl. No. 60/493,515, filed Aug. 8, 2002, Sleeper et al.
(Continued)

*Primary Examiner* — Timothy A Stanis
*Assistant Examiner* — Benjamin M. Kusiak
(74) *Attorney, Agent, or Firm* — Knobbe, Martens, Olson & Bear, LLP

(57) ABSTRACT

Headgear for use with a respiratory mask is described. The headgear can include a continuous and substantially curved elongate member extending in use below a user's nose and at least two headgear straps capable of attachment to the ends of the elongate member. A mask attachment on the elongate member is disposed to sit below or on one of said user's nose, mouth, upper lip and an inlet to the mask. The attachment is capable of receiving the mask.

28 Claims, 21 Drawing Sheets

Related U.S. Application Data

No. 15/088,628, filed on Apr. 1, 2016, now Pat. No. 9,517,317, which is a continuation of application No. 14/887,212, filed on Oct. 19, 2015, now Pat. No. 9,320,866, which is a continuation of application No. 14/812,167, filed on Jul. 29, 2015, now Pat. No. 9,339,624, which is a continuation of application No. 12/633,135, filed on Dec. 8, 2009, now Pat. No. 9,138,555, which is a continuation of application No. 12/307,933, filed as application No. PCT/NZ2007/000185 on Jul. 13, 2007, now Pat. No. 8,443,807.

(51) Int. Cl.
 *A61M 16/16* (2006.01)
 *A61M 16/00* (2006.01)

(52) U.S. Cl.
 CPC ........ *A61M 16/06* (2013.01); *A61M 16/0616* (2014.02); *A61M 16/0622* (2014.02); *A61M 16/0683* (2013.01); *A61M 16/0816* (2013.01); *A61M 16/0825* (2014.02); *A61M 16/16* (2013.01); *A61M 16/161* (2014.02); *A61M 16/0611* (2014.02); *A61M 2016/0039* (2013.01); *A61M 2205/0216* (2013.01); *A61M 2205/3368* (2013.01); *A61M 2205/3653* (2013.01); *A61M 2205/50* (2013.01); *A61M 2210/0618* (2013.01); *A61M 2210/0625* (2013.01)

(58) Field of Classification Search
 CPC ........... A61M 2205/0216; A61M 16/00–0003; A62B 9/04; A62B 18/02–025
 USPC ............ 128/205.25, 206.12, 206.13, 206.18, 128/207.11, 207.17
 See application file for complete search history.

(56) References Cited

U.S. PATENT DOCUMENTS

| | | |
|---|---|---|
| 577,926 A | 3/1897 | Miller |
| 718,470 A | 1/1903 | Jones |
| 751,091 A | 2/1904 | Moran |
| 770,013 A | 9/1904 | Linn |
| 1,635,545 A | 7/1927 | Drager |
| 2,126,755 A | 8/1938 | Dreyfus |
| 2,228,218 A | 1/1941 | Schwartz |
| 2,241,535 A | 5/1941 | Boothby et al. |
| 2,296,150 A | 9/1942 | Dockson et al. |
| 2,353,643 A | 7/1944 | Bulbulian |
| 2,359,506 A | 10/1944 | Battley et al. |
| 2,388,604 A | 11/1945 | Eisenbud |
| 2,452,845 A | 11/1948 | Fisher |
| 2,508,050 A | 5/1950 | Valente |
| 2,693,800 A | 11/1954 | Caldwell |
| 2,738,788 A | 3/1956 | Matheson et al. |
| 2,843,121 A | 7/1958 | Hudson |
| 2,859,748 A | 11/1958 | Hudson |
| 2,875,759 A | 3/1959 | Galleher |
| 2,894,506 A | 7/1959 | Rose |
| 2,939,458 A | 6/1960 | Lundquist |
| 3,424,633 A | 1/1969 | Corrigall et al. |
| 3,490,452 A | 1/1970 | Greenfield |
| 3,599,635 A | 8/1971 | Kenneth |
| 3,682,171 A | 8/1972 | Dali et al. |
| 3,834,682 A | 9/1974 | McPhee |
| 3,850,171 A | 11/1974 | Ball et al. |
| 3,894,562 A | 7/1975 | Mosley et al. |
| 3,972,321 A | 8/1976 | Proctor |
| 3,977,432 A | 8/1976 | Vidal |
| 3,992,720 A | 11/1976 | Nicolinas |
| 4,090,510 A | 5/1978 | Segersten |
| D250,047 S | 10/1978 | Lewis et al. |
| D250,131 S | 10/1978 | Lewis et al. |
| 4,127,130 A | 11/1978 | Naysmith |
| 4,150,464 A | 4/1979 | Tracy |
| D252,322 S | 7/1979 | Johnson |
| 4,201,205 A | 5/1980 | Bartholomew |
| 4,258,710 A | 3/1981 | Reber |
| 4,266,540 A | 5/1981 | Panzik et al. |
| 4,278,082 A | 7/1981 | Blackmer |
| 4,354,488 A | 10/1982 | Bartos |
| 4,367,735 A | 1/1983 | Dali |
| 4,378,011 A | 3/1983 | Warncke et al. |
| 4,437,462 A | 3/1984 | Piljay |
| 4,454,880 A | 6/1984 | Muto et al. |
| 4,574,799 A | 3/1986 | Warncke et al. |
| 4,603,602 A | 8/1986 | Montesi |
| 4,621,632 A | 11/1986 | Bartels et al. |
| 4,644,974 A | 2/1987 | Zingg |
| 4,676,241 A | 6/1987 | Webb et al. |
| D293,613 S | 1/1988 | Wingler |
| 4,753,233 A | 6/1988 | Grimes |
| 4,782,832 A | 11/1988 | Trimble et al. |
| 4,836,200 A | 6/1989 | Clark et al. |
| 4,856,508 A | 8/1989 | Tayebi |
| 4,907,584 A | 3/1990 | McGinnis |
| 4,915,104 A | 4/1990 | Marcy |
| 4,915,105 A | 4/1990 | Lee |
| 4,919,128 A | 4/1990 | Kopala et al. |
| 4,938,209 A | 7/1990 | Fry |
| 4,941,467 A | 7/1990 | Takata |
| 4,944,310 A | 7/1990 | Sullivan |
| D310,431 S | 9/1990 | Bellm |
| 4,958,658 A | 9/1990 | Zajac |
| 4,971,051 A | 11/1990 | Toffolon |
| 4,986,269 A | 1/1991 | Hakkinen |
| 5,010,925 A | 4/1991 | Atkinson et al. |
| 5,016,625 A | 5/1991 | Hsu et al. |
| 5,031,261 A | 7/1991 | Fenner |
| 5,042,478 A | 8/1991 | Kopala et al. |
| D320,677 S | 10/1991 | Kumagai et al. |
| D321,419 S | 11/1991 | Wallace |
| 5,062,421 A | 11/1991 | Burns et al. |
| 5,065,756 A | 11/1991 | Rapoport |
| D322,318 S | 12/1991 | Sullivan et al. |
| 5,074,297 A | 12/1991 | Venegas |
| 5,094,236 A | 3/1992 | Tayebi |
| 5,113,857 A | 5/1992 | Dickerman et al. |
| 5,121,745 A | 6/1992 | Israel et al. |
| 5,148,802 A | 9/1992 | Sanders et al. |
| 5,164,652 A | 11/1992 | Johnson et al. |
| 5,231,979 A | 8/1993 | Rose |
| 5,243,971 A | 9/1993 | Sullivan et al. |
| 5,245,995 A | 9/1993 | Sullivan et al. |
| D340,317 S | 10/1993 | Cole |
| 5,259,377 A | 11/1993 | Schroeder |
| 5,267,556 A | 12/1993 | Feng |
| 5,269,296 A | 12/1993 | Landis et al. |
| 5,315,859 A | 5/1994 | Schommer |
| 5,349,949 A | 9/1994 | Schegerin |
| 5,366,805 A | 11/1994 | Fujiki et al. |
| D354,128 S | 1/1995 | Rinehart |
| D355,484 S | 2/1995 | Rinehart |
| 5,400,776 A | 3/1995 | Bartholomew |
| 5,429,683 A | 7/1995 | Le Mitouard |
| 5,438,979 A | 8/1995 | Johnson et al. |
| 5,441,046 A | 8/1995 | Starr et al. |
| 5,449,206 A | 9/1995 | Lockwood |
| 5,449,234 A | 9/1995 | Gipp et al. |
| 5,458,202 A | 10/1995 | Fellows et al. |
| 5,460,174 A | 10/1995 | Chang |
| 5,461,932 A | 10/1995 | Hall |
| 5,477,852 A | 12/1995 | Landis et al. |
| 5,513,634 A | 5/1996 | Jackson |
| 5,518,802 A | 5/1996 | Colvin et al. |
| 5,533,506 A | 7/1996 | Wood |
| 5,542,128 A | 8/1996 | Lomas |
| 5,551,419 A | 9/1996 | Froehlich et al. |
| 5,558,090 A | 9/1996 | James |
| 5,570,689 A | 11/1996 | Starr et al. |
| 5,588,423 A | 12/1996 | Smith |

(56) References Cited

U.S. PATENT DOCUMENTS

| | | |
|---|---|---|
| 5,595,174 A | 1/1997 | Gwaltney |
| 5,601,078 A | 2/1997 | Schaller et al. |
| D378,610 S | 3/1997 | Reischel et al. |
| 5,649,532 A | 7/1997 | Griffiths |
| 5,657,752 A | 8/1997 | Landis et al. |
| 5,662,101 A | 9/1997 | Ogden et al. |
| 5,664,566 A | 9/1997 | Mcdonald et al. |
| 5,687,715 A | 11/1997 | Landis |
| 5,690,097 A | 11/1997 | Howard et al. |
| 5,724,677 A | 3/1998 | Bryant et al. |
| 5,724,965 A | 3/1998 | Handke et al. |
| 5,752,510 A | 5/1998 | Goldstein |
| 5,755,578 A | 5/1998 | Contant et al. |
| 5,789,660 A | 8/1998 | Kofoed |
| 5,806,727 A | 9/1998 | Joseph |
| 5,807,295 A | 9/1998 | Hutcheon et al. |
| 5,746,201 A | 12/1998 | Kidd |
| 5,857,460 A | 1/1999 | Popitz |
| 5,884,624 A | 3/1999 | Barnett et al. |
| 5,904,278 A | 5/1999 | Barlow et al. |
| 5,918,598 A | 7/1999 | Belfer |
| 5,921,239 A | 7/1999 | McCall et al. |
| 5,924,420 A | 7/1999 | Reischel |
| 5,941,245 A | 8/1999 | Hannah et al. |
| 5,943,473 A | 8/1999 | Levine |
| 5,953,763 A | 9/1999 | Gouget |
| 5,966,745 A | 10/1999 | Schwartz et al. |
| 6,016,804 A | 1/2000 | Gleason et al. |
| 6,017,315 A | 1/2000 | Starr et al. |
| 6,019,101 A | 2/2000 | Cotner et al. |
| 6,021,528 A | 2/2000 | Jurga |
| 6,039,044 A | 3/2000 | Sullivan |
| 6,050,260 A | 4/2000 | Daniell et al. |
| 6,112,746 A | 9/2000 | Kwok et al. |
| 6,116,235 A | 9/2000 | Walters et al. |
| 6,119,693 A | 9/2000 | Kwok et al. |
| 6,119,694 A | 9/2000 | Correa et al. |
| 6,135,109 A | 10/2000 | Blasdell et al. |
| 6,135,432 A | 10/2000 | Hebblewhite et al. |
| 6,192,886 B1 | 2/2001 | Rudolph |
| D440,302 S | 4/2001 | Wolfe |
| 6,272,933 B1 | 8/2001 | Gradon et al. |
| 6,298,850 B1 | 10/2001 | Argraves |
| 6,302,105 B1 | 10/2001 | Wickham et al. |
| 6,341,606 B1 | 1/2002 | Bordewick et al. |
| 6,347,631 B1 | 2/2002 | Hansen et al. |
| D455,891 S | 4/2002 | Biedrzycki |
| 6,398,197 B1 | 6/2002 | Dickinson et al. |
| 6,412,487 B1 | 7/2002 | Gunaratnam et al. |
| 6,412,488 B1 | 7/2002 | Barnett |
| 6,418,928 B1 | 7/2002 | Bordewick et al. |
| 6,427,694 B1 | 8/2002 | Hecker et al. |
| 6,431,172 B1 | 8/2002 | Bordewick |
| 6,435,181 B1 | 8/2002 | Jones, Jr. et al. |
| 6,439,234 B1 | 8/2002 | Curti et al. |
| 6,457,473 B1 | 10/2002 | Brostrom et al. |
| 6,467,483 B1 | 10/2002 | Kopacko et al. |
| 6,470,886 B1 | 10/2002 | Jestrabek-Hart |
| 6,478,026 B1 | 11/2002 | Wood |
| 6,484,725 B1 | 11/2002 | Chi et al. |
| 6,488,664 B1 | 12/2002 | Solomon et al. |
| 6,491,034 B1 | 12/2002 | Gunaratnam et al. |
| 6,513,526 B2 | 2/2003 | Kwok et al. |
| 6,526,978 B2 | 3/2003 | Dominguez |
| 6,530,373 B1 | 3/2003 | Patron et al. |
| 6,561,188 B1 | 5/2003 | Ellis |
| 6,561,190 B1 | 5/2003 | Kwok |
| 6,561,191 B1 | 5/2003 | Kwok |
| 6,581,594 B1 | 6/2003 | Drew et al. |
| 6,581,601 B2 | 6/2003 | Ziaee |
| 6,581,602 B2 | 6/2003 | Kwok et al. |
| 6,584,977 B1 | 7/2003 | Serowski |
| 6,588,424 B2 | 7/2003 | Bardel |
| 6,615,832 B1 | 9/2003 | Chen |
| 6,629,531 B2 | 10/2003 | Gleason et al. |
| 6,631,718 B1 | 10/2003 | Lovell |
| 6,634,358 B2 | 10/2003 | Kwok et al. |
| 6,637,434 B2 | 10/2003 | Noble |
| 6,644,315 B2 | 11/2003 | Ziaee |
| 6,651,658 B1 | 11/2003 | Hill et al. |
| 6,651,663 B2 | 11/2003 | Barnett et al. |
| 6,659,102 B1 | 12/2003 | Sico |
| 6,662,803 B2 | 12/2003 | Gradon et al. |
| 6,668,828 B1 | 12/2003 | Figley et al. |
| D485,905 S | 1/2004 | Moore |
| 6,679,257 B1 | 1/2004 | Robertson et al. |
| 6,679,265 B2 | 1/2004 | Strickland et al. |
| 6,691,707 B1 | 2/2004 | Gunaratnam et al. |
| 6,712,072 B1 | 3/2004 | Lang |
| 6,736,139 B1 | 5/2004 | Wix |
| 6,772,761 B1 | 8/2004 | Rucker, Jr. |
| 6,796,308 B2 | 9/2004 | Gunaratnam et al. |
| 6,817,362 B2 | 11/2004 | Gelinas et al. |
| 6,823,869 B2 | 11/2004 | Raje et al. |
| 6,851,425 B2 | 2/2005 | Jaffre et al. |
| 6,851,428 B2 | 2/2005 | Dennis |
| 6,883,177 B1 | 4/2005 | Ouellette et al. |
| 6,892,729 B2 | 5/2005 | Smith et al. |
| 6,895,965 B2 | 5/2005 | Scarberry et al. |
| 6,907,882 B2 | 6/2005 | Ging et al. |
| 6,918,390 B2 | 7/2005 | Lithgow et al. |
| 6,951,218 B2 | 10/2005 | Gradon et al. |
| 6,953,354 B2 | 10/2005 | Edirisuriya et al. |
| 6,997,187 B2 | 2/2006 | Wood et al. |
| 7,004,165 B1 | 2/2006 | Salcido |
| 7,007,696 B2 | 3/2006 | Palkon et al. |
| 7,021,311 B2 | 4/2006 | Gunaratnam et al. |
| D520,140 S | 5/2006 | Chaggares |
| 7,051,765 B1 | 5/2006 | Kelley |
| 7,066,179 B2 | 6/2006 | Eaton et al. |
| 7,077,126 B2 | 7/2006 | Kummer et al. |
| D526,094 S | 8/2006 | Chen |
| 7,096,864 B1 | 8/2006 | Mayer et al. |
| D533,269 S | 12/2006 | McAuley et al. |
| 7,178,525 B2 | 2/2007 | Matula, Jr. et al. |
| 7,178,528 B2 | 2/2007 | Lau |
| 7,201,169 B2 | 4/2007 | Wilkie et al. |
| 7,207,333 B2 | 4/2007 | Tohara |
| 7,210,481 B1 | 5/2007 | Lovell et al. |
| 7,219,669 B1 | 5/2007 | Lovell et al. |
| 7,225,811 B2 | 6/2007 | Ruiz et al. |
| 7,255,106 B2 | 8/2007 | Gallem et al. |
| 7,261,104 B2 * | 8/2007 | Kiefer ..................... A62B 9/04 128/201.17 |
| 7,287,528 B2 | 10/2007 | Ho et al. |
| 7,290,546 B2 | 11/2007 | Sprinkle et al. |
| 7,296,575 B1 * | 11/2007 | Radney ................. A61M 16/06 128/207.11 |
| 7,318,437 B2 | 1/2008 | Gunaratnam et al. |
| 7,353,827 B2 | 4/2008 | Geist |
| 7,357,136 B2 | 4/2008 | Ho et al. |
| 7,406,966 B2 | 8/2008 | Wondka et al. |
| 7,448,386 B2 | 11/2008 | Ho et al. |
| 7,487,772 B2 | 2/2009 | Ging et al. |
| 7,493,902 B2 | 2/2009 | White et al. |
| D589,139 S | 3/2009 | Guney |
| 7,523,754 B2 | 4/2009 | Lithgow et al. |
| D595,841 S | 7/2009 | McAuley et al. |
| 7,562,658 B2 | 7/2009 | Madaus et al. |
| 7,597,100 B2 | 10/2009 | Ging |
| 7,640,934 B2 | 1/2010 | Zollinger et al. |
| 7,658,189 B2 | 2/2010 | Davidson et al. |
| 7,665,464 B2 | 2/2010 | Kopacko et al. |
| D612,933 S | 3/2010 | Prentice |
| 7,681,575 B2 | 3/2010 | Wixey et al. |
| 7,694,677 B2 | 4/2010 | Tang |
| 7,703,457 B2 | 4/2010 | Barnett et al. |
| 7,708,017 B2 | 5/2010 | Davidson |
| 7,753,051 B2 | 7/2010 | Burrow et al. |
| D623,288 S | 9/2010 | Lubke |
| 7,814,911 B2 | 10/2010 | Bordewick et al. |
| 7,827,990 B1 | 11/2010 | Melidis et al. |
| 7,856,982 B2 | 12/2010 | Matula et al. |
| 7,877,817 B1 | 2/2011 | Ho |

(56) References Cited

U.S. PATENT DOCUMENTS

| | | |
|---|---|---|
| 7,896,003 B2 | 3/2011 | Matula et al. |
| 7,931,024 B2 | 4/2011 | Ho et al. |
| 7,934,501 B2 | 5/2011 | Fu |
| 7,942,150 B2 | 5/2011 | Guney et al. |
| 7,992,560 B2 | 8/2011 | Burton et al. |
| 8,042,539 B2 | 10/2011 | Chandran et al. |
| 8,042,541 B2 | 10/2011 | Amarasinghe et al. |
| 8,109,271 B2 | 2/2012 | Vandine et al. |
| 8,136,524 B2 | 3/2012 | Ging et al. |
| 8,136,525 B2 | 3/2012 | Lubke et al. |
| 8,171,933 B2 | 5/2012 | Xue et al. |
| D661,796 S | 6/2012 | Andrews et al. |
| 8,245,711 B2 | 8/2012 | Matula et al. |
| 8,371,302 B2 | 2/2013 | Ging et al. |
| 8,397,727 B2 | 3/2013 | Ng et al. |
| 8,443,807 B2 | 5/2013 | McAuley et al. |
| D686,313 S | 7/2013 | Matula et al. |
| 8,479,726 B2 | 7/2013 | McAuley |
| 8,479,741 B2 | 7/2013 | McAuley et al. |
| 8,567,404 B2 | 10/2013 | Davidson et al. |
| 8,631,793 B2 | 1/2014 | Omura et al. |
| 8,631,799 B2 | 1/2014 | Davenport |
| 8,636,005 B2 | 1/2014 | Gradon et al. |
| 8,701,667 B1 | 4/2014 | Ho et al. |
| 8,714,157 B2 | 5/2014 | McAuley et al. |
| 8,720,444 B2 | 5/2014 | Chang |
| 8,757,157 B2 | 6/2014 | Price et al. |
| 8,783,257 B2 | 7/2014 | McAuley et al. |
| 8,869,797 B2 | 10/2014 | Davidson et al. |
| 8,869,798 B2 | 10/2014 | Wells et al. |
| 8,875,709 B2 | 11/2014 | Davidson et al. |
| 8,944,061 B2 | 2/2015 | D'Souza et al. |
| 8,950,404 B2 | 2/2015 | Formica et al. |
| 8,960,196 B2 | 2/2015 | Henry |
| 9,010,331 B2 | 4/2015 | Lang et al. |
| 9,027,556 B2 | 5/2015 | Ng et al. |
| 9,032,955 B2 | 5/2015 | Lubke et al. |
| 9,032,956 B2 | 5/2015 | Scheiner et al. |
| 9,072,852 B2 | 7/2015 | McAuley et al. |
| 9,095,673 B2 | 8/2015 | Barlow et al. |
| 9,119,929 B2 | 9/2015 | McAuley et al. |
| 9,119,931 B2 | 9/2015 | D'Souza et al. |
| 9,138,555 B2 | 9/2015 | McAuley et al. |
| 9,149,596 B2 | 10/2015 | Valcic et al. |
| 9,186,474 B1 | 11/2015 | Rollins |
| 9,242,062 B2 | 1/2016 | Melidis et al. |
| 9,292,799 B2 | 3/2016 | McAuley et al. |
| 9,295,799 B2 | 3/2016 | McAuley et al. |
| 9,302,065 B2 | 4/2016 | Smith et al. |
| 9,320,566 B1 | 4/2016 | Alston, Jr. |
| 9,320,866 B2 | 4/2016 | McAuley et al. |
| 9,333,315 B2 | 5/2016 | McAuley et al. |
| 9,339,622 B2 | 5/2016 | McAuley et al. |
| 9,339,624 B2 | 5/2016 | McAuley |
| 9,375,545 B2 | 6/2016 | Darkin et al. |
| 9,381,316 B2 | 7/2016 | Ng et al. |
| 9,457,162 B2 | 10/2016 | Ging et al. |
| 9,486,601 B2 | 11/2016 | Stallard et al. |
| 9,517,317 B2 | 12/2016 | McAuley et al. |
| 9,522,246 B2 | 12/2016 | Frater et al. |
| 9,539,405 B2 | 1/2017 | McAuley et al. |
| 9,550,038 B2 | 1/2017 | McAuley et al. |
| 9,561,338 B2 | 2/2017 | McAuley et al. |
| 9,561,339 B2 | 2/2017 | McAuley et al. |
| 9,744,385 B2 | 8/2017 | Henry et al. |
| 9,884,160 B2 | 2/2018 | McAuley et al. |
| 9,901,699 B2 | 2/2018 | Veliss et al. |
| 9,901,700 B2 | 2/2018 | McAuley et al. |
| 9,907,925 B2 | 3/2018 | McAuley et al. |
| 9,974,914 B2 | 5/2018 | McAuley |
| 10,080,856 B2 | 9/2018 | McLaren et al. |
| 10,137,271 B2 | 11/2018 | McAuley et al. |
| 10,201,678 B2 | 2/2019 | Guney et al. |
| 10,252,015 B2 | 4/2019 | McAuley et al. |
| 10,258,757 B2 | 4/2019 | Allan et al. |
| 10,272,218 B2 | 4/2019 | McAuley et al. |
| 10,328,226 B2 | 6/2019 | Allan et al. |
| 10,363,387 B2 | 7/2019 | Allan et al. |
| 10,384,029 B2 | 8/2019 | McAuley et al. |
| 10,413,694 B2 | 9/2019 | Allan et al. |
| 10,463,825 B2 | 11/2019 | McAuley et al. |
| 2001/0017134 A1 | 8/2001 | Bahr |
| 2001/0020474 A1 | 9/2001 | Hecker et al. |
| 2001/0029952 A1 | 10/2001 | Curran |
| 2002/0005198 A1 | 1/2002 | Kwok et al. |
| 2002/0014241 A1 | 2/2002 | Gradon et al. |
| 2002/0020416 A1 | 2/2002 | Namey |
| 2002/0026934 A1 | 3/2002 | Lithgow et al. |
| 2002/0029780 A1 | 3/2002 | Frater et al. |
| 2002/0039867 A1 | 4/2002 | Curro et al. |
| 2002/0046755 A1 | 4/2002 | Voss |
| 2002/0053347 A1 | 5/2002 | Ziaee |
| 2002/0059935 A1 | 5/2002 | Wood |
| 2002/0069467 A1 | 6/2002 | Immediato et al. |
| 2002/0096176 A1 | 7/2002 | Gunaratnam et al. |
| 2002/0096178 A1 | 7/2002 | Ziaee |
| 2002/0100474 A1 | 8/2002 | Kellner et al. |
| 2002/0100479 A1 | 8/2002 | Scarberry et al. |
| 2002/0108613 A1 | 8/2002 | Gunaratnam et al. |
| 2003/0005509 A1 | 1/2003 | Kelzer |
| 2003/0005931 A1 | 1/2003 | Jaffre et al. |
| 2003/0005933 A1 | 1/2003 | Izuchukwu |
| 2003/0019495 A1 | 1/2003 | Palkon et al. |
| 2003/0019496 A1 | 1/2003 | Kopacko et al. |
| 2003/0029454 A1 | 2/2003 | Gelinas et al. |
| 2003/0047185 A1 | 3/2003 | Olsen et al. |
| 2003/0075180 A1 | 4/2003 | Raje |
| 2003/0075182 A1 | 4/2003 | Heidmann et al. |
| 2003/0079749 A1 | 5/2003 | Strickland et al. |
| 2003/0084996 A1 | 5/2003 | Alberg et al. |
| 2003/0089373 A1 | 5/2003 | Gradon et al. |
| 2003/0094177 A1 | 5/2003 | Smith et al. |
| 2003/0121519 A1 | 7/2003 | Estes et al. |
| 2003/0149384 A1 | 8/2003 | Davis et al. |
| 2003/0164170 A1 | 9/2003 | Drew et al. |
| 2003/0172936 A1 | 9/2003 | Wilkie et al. |
| 2003/0196655 A1 | 10/2003 | Ging et al. |
| 2003/0196656 A1 | 10/2003 | Moore |
| 2003/0196658 A1 | 10/2003 | Ging et al. |
| 2003/0196659 A1 | 10/2003 | Gradon et al. |
| 2003/0196664 A1 | 10/2003 | Jacobson |
| 2003/0200970 A1 | 10/2003 | Stenzler et al. |
| 2003/0217746 A1 | 11/2003 | Gradon et al. |
| 2003/0221691 A1 | 12/2003 | Biener |
| 2004/0011087 A1 | 1/2004 | Rebouillat et al. |
| 2004/0025882 A1 | 2/2004 | Madaus et al. |
| 2004/0035427 A1 | 2/2004 | Bordewick et al. |
| 2004/0065328 A1 | 4/2004 | Amarasinghe et al. |
| 2004/0067333 A1 | 4/2004 | Amarasinghe |
| 2004/0092999 A1 | 5/2004 | Lojewski |
| 2004/0094157 A1 | 5/2004 | Dantanarayana et al. |
| 2004/0107968 A1 | 6/2004 | Griffiths |
| 2004/0112377 A1 | 6/2004 | Amarasinghe et al. |
| 2004/0112384 A1 | 6/2004 | Lithgow et al. |
| 2004/0112385 A1 | 6/2004 | Drew |
| 2004/0118212 A1 | 6/2004 | Orr |
| 2004/0118406 A1 | 6/2004 | Lithgow |
| 2004/0118412 A1 | 6/2004 | Piletti-Reyes |
| 2004/0139973 A1 | 7/2004 | Wright |
| 2004/0149280 A1 | 8/2004 | Semeniuk |
| 2004/0182398 A1 | 9/2004 | Sprinkle et al. |
| 2004/0211427 A1 | 10/2004 | Jones et al. |
| 2004/0221850 A1 | 11/2004 | Ging et al. |
| 2004/0226566 A1 | 11/2004 | Gunaratnam et al. |
| 2004/0255949 A1 | 12/2004 | Lang et al. |
| 2004/0261797 A1 | 12/2004 | White |
| 2005/0011521 A1 | 1/2005 | Sprinkle et al. |
| 2005/0011524 A1 | 1/2005 | Thomlinson et al. |
| 2005/0016532 A1 | 1/2005 | Farrell |
| 2005/0028822 A1 | 2/2005 | Sleeper et al. |
| 2005/0033247 A1 | 2/2005 | Thompson |
| 2005/0045182 A1 | 3/2005 | Wood et al. |
| 2005/0051177 A1 | 3/2005 | Wood |
| 2005/0066976 A1 | 3/2005 | Wondka |

(56) References Cited

U.S. PATENT DOCUMENTS

| | | |
|---|---|---|
| 2005/0076913 A1 | 4/2005 | Ho et al. |
| 2005/0092327 A1 | 5/2005 | Fini et al. |
| 2005/0098183 A1 | 5/2005 | Nash et al. |
| 2005/0121037 A1 | 6/2005 | Wood |
| 2005/0133038 A1 | 6/2005 | Rutter |
| 2005/0150497 A1 | 7/2005 | Eifler et al. |
| 2005/0155604 A1 | 7/2005 | Ging et al. |
| 2005/0172969 A1* | 8/2005 | Ging ................ A61M 16/0683 128/206.24 |
| 2005/0199239 A1 | 9/2005 | Lang et al. |
| 2005/0199242 A1 | 9/2005 | Matula et al. |
| 2005/0205096 A1 | 9/2005 | Matula |
| 2005/0235999 A1 | 10/2005 | Wood et al. |
| 2005/0241644 A1 | 11/2005 | Guney et al. |
| 2006/0032504 A1 | 2/2006 | Burton et al. |
| 2006/0042629 A1 | 3/2006 | Geist |
| 2006/0042632 A1 | 3/2006 | Bishop et al. |
| 2006/0054169 A1 | 3/2006 | Han et al. |
| 2006/0060200 A1* | 3/2006 | Ho ................ A61M 16/0683 128/206.24 |
| 2006/0076019 A1 | 4/2006 | Ho |
| 2006/0081250 A1 | 4/2006 | Bordewick et al. |
| 2006/0081256 A1 | 4/2006 | Palmer |
| 2006/0096598 A1 | 5/2006 | Ho et al. |
| 2006/0102185 A1 | 5/2006 | Drew et al. |
| 2006/0107958 A1 | 5/2006 | Sleeper |
| 2006/0118117 A1 | 6/2006 | Berthon-Jones et al. |
| 2006/0124131 A1 | 6/2006 | Chandran |
| 2006/0130844 A1 | 6/2006 | Ho et al. |
| 2006/0137690 A1 | 6/2006 | Gunaratnam et al. |
| 2006/0169286 A1 | 8/2006 | Eifler et al. |
| 2006/0174887 A1* | 8/2006 | Chandran ............ A61M 16/06 128/206.11 |
| 2006/0196511 A1 | 9/2006 | Lau et al. |
| 2006/0201514 A1 | 9/2006 | Jones et al. |
| 2006/0207599 A1 | 9/2006 | Busch |
| 2006/0225740 A1 | 10/2006 | Eaton et al. |
| 2006/0231103 A1 | 10/2006 | Matula et al. |
| 2006/0237017 A1 | 10/2006 | Davidson et al. |
| 2006/0237018 A1 | 10/2006 | McAuley et al. |
| 2006/0249159 A1 | 11/2006 | Ho |
| 2006/0254593 A1 | 11/2006 | Chang |
| 2006/0266361 A1 | 11/2006 | Hernandez |
| 2006/0283458 A1 | 12/2006 | Woodard |
| 2006/0283459 A1 | 12/2006 | Geiselhart et al. |
| 2006/0283461 A1* | 12/2006 | Lubke ............... A61M 16/0816 128/207.11 |
| 2007/0000492 A1 | 1/2007 | Hansel et al. |
| 2007/0010786 A1 | 1/2007 | Casey et al. |
| 2007/0044804 A1 | 3/2007 | Matula et al. |
| 2007/0062536 A1 | 3/2007 | McAuley |
| 2007/0089749 A1 | 4/2007 | Ho et al. |
| 2007/0107733 A1 | 5/2007 | Ho |
| 2007/0125384 A1 | 6/2007 | Zollinger et al. |
| 2007/0125385 A1 | 6/2007 | Ho et al. |
| 2007/0125387 A1 | 6/2007 | Zollinger et al. |
| 2007/0137653 A1 | 6/2007 | Wood |
| 2007/0142785 A1 | 6/2007 | Lundgaard et al. |
| 2007/0157353 A1 | 7/2007 | Guney et al. |
| 2007/0163594 A1 | 7/2007 | Ho |
| 2007/0163600 A1 | 7/2007 | Hoffman |
| 2007/0174952 A1 | 8/2007 | Jacob |
| 2007/0175480 A1 | 8/2007 | Gradon et al. |
| 2007/0209663 A1 | 9/2007 | Marque et al. |
| 2007/0215161 A1 | 9/2007 | Frater et al. |
| 2007/0221227 A1 | 9/2007 | Ho |
| 2007/0227541 A1 | 10/2007 | Van Den |
| 2007/0272249 A1 | 11/2007 | Chandran |
| 2007/0295335 A1 | 12/2007 | Nashed |
| 2008/0035152 A1 | 2/2008 | Ho et al. |
| 2008/0041388 A1 | 2/2008 | McAuley et al. |
| 2008/0041393 A1 | 2/2008 | Bracken |
| 2008/0047560 A1 | 2/2008 | Veliss et al. |
| 2008/0060648 A1 | 3/2008 | Thornton et al. |
| 2008/0060653 A1 | 3/2008 | Hallett et al. |
| 2008/0060657 A1 | 3/2008 | McAuley et al. |
| 2008/0083412 A1 | 4/2008 | Henry et al. |
| 2008/0092905 A1 | 4/2008 | Gunaratnam |
| 2008/0099024 A1 | 5/2008 | Gunaratnam et al. |
| 2008/0105257 A1 | 5/2008 | Klasek et al. |
| 2008/0110464 A1 | 5/2008 | Davidson et al. |
| 2008/0135050 A1* | 6/2008 | Hitchcock ......... A61M 16/0683 128/207.11 |
| 2008/0142019 A1 | 6/2008 | Lewis |
| 2008/0149104 A1 | 6/2008 | Ho |
| 2008/0171737 A1 | 7/2008 | Fensome |
| 2008/0178875 A1 | 7/2008 | Henry |
| 2008/0178886 A1 | 7/2008 | Lieberman et al. |
| 2008/0190432 A1 | 8/2008 | Blochlinger et al. |
| 2008/0190436 A1 | 8/2008 | Jaffe et al. |
| 2008/0196728 A1 | 8/2008 | Ho |
| 2008/0210241 A1 | 9/2008 | Schulz et al. |
| 2008/0223370 A1 | 9/2008 | Kim |
| 2008/0236586 A1 | 10/2008 | Mcdonald et al. |
| 2008/0257354 A1 | 10/2008 | Davidson |
| 2008/0264422 A1 | 10/2008 | Fishman |
| 2008/0271739 A1 | 11/2008 | Facer et al. |
| 2008/0276937 A1 | 11/2008 | Davidson et al. |
| 2008/0302366 A1 | 12/2008 | McGinnis et al. |
| 2008/0314388 A1 | 12/2008 | Brambilla et al. |
| 2008/0319334 A1 | 12/2008 | Yamamori |
| 2009/0014007 A1 | 1/2009 | Brambilla et al. |
| 2009/0032024 A1 | 2/2009 | Burz et al. |
| 2009/0044808 A1 | 2/2009 | Guney et al. |
| 2009/0078267 A1 | 3/2009 | Burz et al. |
| 2009/0107504 A1 | 4/2009 | McAuley et al. |
| 2009/0114227 A1 | 5/2009 | Gunaratnam et al. |
| 2009/0120442 A1 | 5/2009 | Ho |
| 2009/0126739 A1* | 5/2009 | Ng ................ A61M 16/0683 128/205.25 |
| 2009/0133697 A1 | 5/2009 | Kwok et al. |
| 2009/0139527 A1 | 6/2009 | Ng et al. |
| 2009/0145429 A1 | 6/2009 | Ging et al. |
| 2009/0151729 A1* | 6/2009 | Judson ............ A61M 16/0633 128/207.13 |
| 2009/0173349 A1 | 7/2009 | Hernandez et al. |
| 2009/0183734 A1 | 7/2009 | Kwok et al. |
| 2009/0183739 A1 | 7/2009 | Wondka |
| 2009/0211583 A1* | 8/2009 | Carroll ............ A61M 16/0683 128/206.27 |
| 2009/0223519 A1 | 9/2009 | Eifler et al. |
| 2009/0320842 A1 | 12/2009 | Doherty |
| 2010/0000538 A1 | 1/2010 | Edwards et al. |
| 2010/0000539 A1 | 1/2010 | Woodard |
| 2010/0000543 A1 | 1/2010 | Berthon-Jones et al. |
| 2010/0051031 A1 | 3/2010 | Lustenberger et al. |
| 2010/0051034 A1 | 3/2010 | Howard |
| 2010/0083969 A1* | 4/2010 | Crumblin ............ A61M 16/06 128/206.21 |
| 2010/0108072 A1 | 5/2010 | D'Souza |
| 2010/0132717 A1 | 6/2010 | Davidson et al. |
| 2010/0154798 A1 | 6/2010 | Henry et al. |
| 2010/0170516 A1 | 7/2010 | Grane |
| 2010/0199992 A1 | 8/2010 | Ho |
| 2010/0229868 A1 | 9/2010 | Rummery et al. |
| 2010/0229872 A1 | 9/2010 | Ho |
| 2010/0258132 A1 | 10/2010 | Moore |
| 2010/0258136 A1 | 10/2010 | Doherty et al. |
| 2010/0294281 A1 | 11/2010 | Ho |
| 2010/0307502 A1 | 12/2010 | Rummery et al. |
| 2010/0313891 A1 | 12/2010 | Veliss et al. |
| 2010/0319700 A1 | 12/2010 | Ng et al. |
| 2010/0326445 A1 | 12/2010 | Veliss et al. |
| 2011/0067704 A1 | 3/2011 | Kooij |
| 2011/0072553 A1 | 3/2011 | Ho |
| 2011/0088699 A1 | 4/2011 | Skipper |
| 2011/0126838 A1 | 6/2011 | Alberici |
| 2011/0146685 A1 | 6/2011 | Allan et al. |
| 2011/0162654 A1 | 7/2011 | Carroll |
| 2011/0232649 A1 | 9/2011 | Collazo et al. |
| 2011/0259337 A1* | 10/2011 | Hitchcock ......... A61M 16/0875 128/207.11 |
| 2011/0265796 A1 | 11/2011 | Amarasinghe et al. |
| 2011/0290253 A1 | 12/2011 | McAuley |

(56) References Cited

U.S. PATENT DOCUMENTS

| | | |
|---|---|---|
| 2012/0125339 A1 | 5/2012 | Ho et al. |
| 2012/0132208 A1 | 5/2012 | Judson et al. |
| 2012/0132209 A1 | 5/2012 | Rummery |
| 2012/0138061 A1 | 6/2012 | Dravitzki et al. |
| 2012/0204879 A1 | 8/2012 | Cariola et al. |
| 2012/0285457 A1 | 11/2012 | Mansour et al. |
| 2012/0304999 A1 | 12/2012 | Swift et al. |
| 2012/0318265 A1 | 12/2012 | Amirav et al. |
| 2013/0133659 A1 | 5/2013 | Ng et al. |
| 2013/0133664 A1 | 5/2013 | Startare |
| 2013/0152918 A1 | 6/2013 | Rummery et al. |
| 2013/0160769 A1 | 6/2013 | Ng et al. |
| 2014/0026888 A1 | 1/2014 | Matula |
| 2014/0083428 A1 | 3/2014 | Rothermel et al. |
| 2014/0083430 A1 | 3/2014 | Matula, Jr. et al. |
| 2014/0137870 A1 | 5/2014 | Barlow et al. |
| 2014/0261432 A1 | 9/2014 | Eves et al. |
| 2014/0311492 A1 | 10/2014 | Stuebiger et al. |
| 2014/0338672 A1 | 11/2014 | D'Souza et al. |
| 2015/0033457 A1 | 2/2015 | Tryner et al. |
| 2015/0090266 A1 | 4/2015 | Melidis et al. |
| 2015/0246198 A1 | 9/2015 | Bearne et al. |
| 2015/0335846 A1 | 11/2015 | Romagnoli et al. |
| 2015/0352308 A1 | 12/2015 | Cullen et al. |
| 2015/0374944 A1 | 12/2015 | Edwards et al. |
| 2016/0001028 A1 | 1/2016 | McAuley et al. |
| 2016/0008558 A1 | 1/2016 | Huddart et al. |
| 2016/0015922 A1 | 1/2016 | Chodkowski et al. |
| 2016/0038707 A1 | 2/2016 | Allan et al. |
| 2016/0051786 A1 | 2/2016 | McAuley et al. |
| 2016/0213873 A1 | 7/2016 | McAuley et al. |
| 2016/0213874 A1 | 7/2016 | Davidson et al. |
| 2016/0296720 A1 | 10/2016 | Henry et al. |
| 2017/0143925 A1 | 5/2017 | McAuley et al. |
| 2017/0239438 A1 | 8/2017 | McAuley et al. |
| 2017/0246411 A1 | 8/2017 | Mashal et al. |
| 2017/0296770 A1 | 10/2017 | Gunaratnam et al. |
| 2017/0304574 A1 | 10/2017 | McAuley et al. |
| 2017/0368288 A1 | 12/2017 | Stephens et al. |
| 2018/0250258 A1 | 9/2018 | Olsen et al. |
| 2018/0256844 A1 | 9/2018 | Galgali et al. |
| 2019/0001095 A1 | 1/2019 | Rose et al. |
| 2019/0030273 A1 | 1/2019 | McAuley et al. |
| 2019/0232010 A1 | 8/2019 | Mcauley et al. |
| 2020/0016357 A1 | 1/2020 | McAuley et al. |
| 2020/0046928 A1 | 3/2020 | Allan |
| 2020/0108219 A1 | 4/2020 | McAuley et al. |
| 2020/0164169 A1 | 5/2020 | McAuley et al. |
| 2020/0171260 A1 | 6/2020 | McLaren |
| 2020/0197644 A1 | 6/2020 | McAuley et al. |
| 2020/0268997 A1 | 8/2020 | McAuley et al. |
| 2021/0008319 A1 | 1/2021 | McAuley et al. |
| 2021/0228829 A1 | 7/2021 | McAuley et al. |

FOREIGN PATENT DOCUMENTS

| | | |
|---|---|---|
| CA | 2648690 | 11/2007 |
| CD | 000966064-0001 | 9/2008 |
| CD | 000966064-0002 | 9/2008 |
| CD | 000966064-0003 | 9/2008 |
| CD | 000966064-0004 | 9/2008 |
| CD | 000966064-0017 | 9/2008 |
| CN | 2172538 | 7/1994 |
| CN | 1780265 | 12/2005 |
| CN | 1751149 | 3/2006 |
| CN | 1784250 | 6/2006 |
| CN | 1901961 | 1/2007 |
| CN | 1905917 | 1/2007 |
| CN | 101115521 | 1/2008 |
| CN | 100502972 | 6/2009 |
| CN | 101516300 | 8/2009 |
| CN | 101541380 | 9/2009 |
| CN | 101991897 | 3/2011 |
| DE | 895692 | 11/1953 |
| DE | 29723101 U1 | 7/1998 |
| DE | 19603949 | 11/1998 |
| DE | 10312881 | 5/2004 |
| DE | 102005041717 | 4/2006 |
| DE | 102006011151 | 9/2007 |
| DE | 10 2009 016150 | 10/2010 |
| EP | 0 350 322 | 1/1990 |
| EP | 0 427 474 | 5/1991 |
| EP | 0 462 701 | 12/1991 |
| EP | 0 747 078 | 12/1996 |
| EP | 1 099 452 | 5/2001 |
| EP | 0 830 180 | 3/2002 |
| EP | 1 258 266 | 11/2002 |
| EP | 1 488 820 | 12/2004 |
| EP | 1 582 231 | 10/2005 |
| EP | 2 042 209 | 4/2009 |
| EP | 2 130 563 | 12/2009 |
| EP | 2 145 645 | 1/2010 |
| EP | 1 753 495 | 9/2010 |
| EP | 1 481 702 | 9/2012 |
| EP | 2 749 176 | 7/2014 |
| EP | 1 646 910 | 8/2015 |
| EP | 2 022 528 | 3/2016 |
| EP | 2 451 518 | 10/2017 |
| FR | 2658725 | 8/1991 |
| FR | 2749176 | 12/1997 |
| GB | 190224431 | 12/1902 |
| GB | 880824 | 10/1961 |
| GB | 979357 | 1/1965 |
| GB | 1467828 | 3/1977 |
| GB | 2133275 | 7/1984 |
| GB | 2173274 | 10/1986 |
| GB | 2186801 | 8/1987 |
| JP | 62-024721 | 2/1987 |
| JP | H09-010311 | 1/1997 |
| JP | 2000-325481 | 11/2000 |
| JP | 2004-016488 | 1/2004 |
| JP | 2005-529687 | 10/2005 |
| JP | 2005-537906 | 12/2005 |
| JP | 2007-516750 | 6/2007 |
| NZ | 531332 | 2/2004 |
| NZ | 534606 | 8/2004 |
| NZ | 528029 | 3/2005 |
| NZ | 548575 | 7/2006 |
| NZ | 551103 | 11/2006 |
| WO | WO 82/003548 | 10/1982 |
| WO | WO 97/32494 | 9/1997 |
| WO | WO 98/04310 | 2/1998 |
| WO | WO 98/04311 | 2/1998 |
| WO | WO 98/018514 | 5/1998 |
| WO | WO 98/024499 | 6/1998 |
| WO | WO 98/048878 | 11/1998 |
| WO | WO 98/57691 | 12/1998 |
| WO | WO 99/04842 | 2/1999 |
| WO | WO 99/43375 | 9/1999 |
| WO | WO 99/058181 | 11/1999 |
| WO | WO 99/058198 | 11/1999 |
| WO | WO 00/050122 | 8/2000 |
| WO | WO 00/057942 | 10/2000 |
| WO | WO 00/069497 | 11/2000 |
| WO | WO 00/74509 | 12/2000 |
| WO | WO 00/074758 | 12/2000 |
| WO | WO 00/078384 | 12/2000 |
| WO | WO 01/00266 | 1/2001 |
| WO | WO 01/32250 | 5/2001 |
| WO | WO 01/041854 | 6/2001 |
| WO | WO 01/058293 | 8/2001 |
| WO | WO 01/062326 | 8/2001 |
| WO | WO 01/94721 | 12/2001 |
| WO | WO 01/97892 | 12/2001 |
| WO | WO 01/097892 | 12/2001 |
| WO | WO 01/097893 | 12/2001 |
| WO | WO 02/005883 | 1/2002 |
| WO | WO 02/011804 | 2/2002 |
| WO | WO 02/047749 | 6/2002 |
| WO | WO 02/074372 | 9/2002 |
| WO | WO 03/035156 | 5/2003 |
| WO | WO 03/092755 | 11/2003 |
| WO | WO 04/007010 | 1/2004 |
| WO | WO 04/096332 | 1/2004 |

(56) References Cited

FOREIGN PATENT DOCUMENTS

| | | |
|---|---|---|
| WO | WO 04/012803 | 2/2004 |
| WO | WO 04/022147 | 3/2004 |
| WO | WO 04/030736 | 4/2004 |
| WO | WO 04/041341 | 5/2004 |
| WO | WO 04/041342 | 5/2004 |
| WO | WO 04/071565 | 8/2004 |
| WO | WO 04/073777 | 9/2004 |
| WO | WO 04/073778 | 9/2004 |
| WO | WO 05/010608 | 2/2005 |
| WO | WO 05/016403 | 2/2005 |
| WO | WO 05/018523 | 3/2005 |
| WO | WO 05/021075 | 3/2005 |
| WO | WO 05/051468 | 6/2005 |
| WO | WO 05/063326 | 7/2005 |
| WO | WO 05/063328 | 7/2005 |
| WO | WO 05/079726 | 9/2005 |
| WO | WO 05/086943 | 9/2005 |
| WO | WO 05/086946 | 9/2005 |
| WO | WO 05/097247 | 10/2005 |
| WO | WO 05/123166 | 12/2005 |
| WO | WO 06/000046 | 1/2006 |
| WO | WO 06/050559 | 5/2006 |
| WO | WO 06/069415 | 7/2006 |
| WO | WO 06/074513 | 7/2006 |
| WO | WO 06/074514 | 7/2006 |
| WO | WO 06/074515 | 7/2006 |
| WO | WO 06/096924 | 9/2006 |
| WO | WO 06/130903 | 12/2006 |
| WO | WO 06/138346 | 12/2006 |
| WO | WO 06/138416 | 12/2006 |
| WO | WO 07/006089 | 1/2007 |
| WO | WO 07/009182 | 1/2007 |
| WO | WO 07/021777 | 2/2007 |
| WO | WO 07/022562 | 3/2007 |
| WO | WO 07/041751 | 4/2007 |
| WO | WO 07/041786 | 4/2007 |
| WO | WO 07/045008 | 4/2007 |
| WO | WO 07/048174 | 5/2007 |
| WO | WO 07/053878 | 5/2007 |
| WO | WO 07/114492 | 10/2007 |
| WO | WO 07/147088 | 12/2007 |
| WO | WO 08/007985 | 1/2008 |
| WO | WO 08/011682 | 1/2008 |
| WO | WO 08/014543 | 2/2008 |
| WO | WO 08/030831 | 3/2008 |
| WO | WO 08/036625 | 3/2008 |
| WO | WO 08/060295 | 5/2008 |
| WO | WO 08/068966 | 6/2008 |
| WO | WO 08/070929 | 6/2008 |
| WO | WO 08/106716 | 9/2008 |
| WO | WO 08/148086 | 12/2008 |
| WO | WO 09/026627 | 3/2009 |
| WO | WO 09/022248 | 4/2009 |
| WO | WO 09/052560 | 4/2009 |
| WO | WO 09/059353 | 5/2009 |
| WO | WO 09/092057 | 7/2009 |
| WO | WO 09/139647 | 11/2009 |
| WO | WO 10/066004 | 6/2010 |
| WO | WO 10/073142 | 7/2010 |
| WO | WO 10/131189 | 11/2010 |
| WO | WO 10/135785 | 12/2010 |
| WO | WO 11/014931 | 2/2011 |
| WO | WO 11/059346 | 5/2011 |
| WO | WO 11/060479 | 5/2011 |
| WO | WO 11/077254 | 6/2011 |
| WO | WO 12/040791 | 4/2012 |
| WO | WO 12/045127 | 4/2012 |
| WO | WO 12/052902 | 4/2012 |
| WO | WO 12/143822 | 10/2012 |
| WO | WO 14/020469 | 2/2014 |
| WO | WO 14/109749 | 7/2014 |
| WO | WO 14/175752 | 10/2014 |
| WO | WO 14/175753 | 10/2014 |
| WO | WO 15/033287 | 3/2015 |
| WO | WO 16/000040 | 1/2016 |
| WO | WO 17/049356 | 3/2017 |
| WO | WO 17/049357 | 3/2017 |
| WO | WO 18/007966 | 1/2018 |
| WO | WO 18/064712 | 4/2018 |

OTHER PUBLICATIONS

U.S. Appl. No. 60/496,059, filed Aug. 18, 2003, Ho et al.
U.S. Appl. No. 60/529,696, filed Dec. 16, 2003, Lithgow et al.
U.S. Appl. No. 61/064,406, filed Mar. 4, 2008, Wehbeh.
U.S. Appl. No. 61/071,893, filed May 22, 2008, Wehbeh et al.
U.S. Appl. No. 61/136,617, filed Sep. 19, 2008, Wehbeh et al.
Fisher & Paykel HC200 Series Nasal CPAP Blower & Heated Humidifier User Manual, 17 pp., May 1998.
Fisher & Paykel Healthcare, FlexiFit™ 431 Full Face Mask, specification sheet, 2004, 2 pp.
Fisher & Paykel MR810 Manual, Rev. C, 2004, 43 pp.
HomeDepot.com—Ring Nut Sales Page (Retrieved Oct. 16, 2015 from http://www.homedepot.com/p/Everbilt-1-2-in-Galvanized-HexNut-804076/20464- 7893), 4 pp.
Malloy, 1994, Plastic Part Design for Injection Molding, Hanswer Gardner Publications, Inc, Cincinnati, OH, 14 pp.
Merriam-Webster's Collegiate Dictionary, Eleventh Edition, 2004, pp. 703, 905, 1074, 1184.
Philips Respironics 'System One Heated Humidifier—User Manual', 2011, pp. 1-16, [retrieved on Nov. 25, 2013] from the internet: URL: http://www.cpapxchange.com/cpap-machines-biap-machines/system-one-60-seri- es-cpap-humidifier-manual.pdf front cover, pp. 3-4 and 6.
ResMed Exhibit, FlexiFit™ 431, product brochure, web pages (Wayback Machine), 2006, 23 pp.
ResMed Origins Brochure (Retrieved Apr. 17, 2016 from http://www.resmed.com/us/dam/documents/articles/resmedorigins.pdf), 64 pp.
ResMed Ultra Mirage™ Full Face Mask, product brochure, 2004, 2 pp.
ResMed Ultra Mirage™ Full Face Mask, product brochure, web pages (Wayback Machine), 2006, 9 pp.
ResMed, Jun. 29, 1997, Mask Frames (Source: Wayback Machine Internet Archive); http://web.archive.org/web/19970629053430/http://www.resmed.com- /maskframes/mask.htm, 2 pp.
ResMed, Mirage Swift™ Nasal Pillows System from ResMed, product brochure, 2004, 6 pp.
ResMed, Mirage Swift™ Nasal Pillows System: User's Guide, product brochure, 2004, 11 pp.
ResMed, Mirage Vista™ Nasal Mask: Components Card, product brochure, 2005, 1 p.
The American Heritage Dictionary of the English Language, Fourth Edition, 2006, pp. 1501, 1502, 1650.
WeddingBands.com—Men's Wedding Ring Shopping Page (Retrieved Oct. 16, 2015 from http://www.weddingbands.com/ProductPop.sub.--wedding.sub.--band- s.sub.--metal/48214W.html), 3 pp.
Australian Examination Report in patent application No. 2012265597 dated Dec. 19, 2013, 5 pages.
Australian Examination Report in patent application No. 2015201920, dated Jul. 20, 2015, 3 pages.
Australian Examination Report in patent application No. 2007273324, dated May 22, 2012, 3 pages.
Australian Examination Report in patent application No. 2010241390, dated Jan. 9, 2015, 4 pages.
Australian Examination Report in patent application No. 2010246985, dated Mar. 4, 2014, 5 pages.
Australian Examination Report in patent application No. 2015202814, dated Aug. 14, 2015, 8 pages.
Australian Examination Report in patent application No. 2016202799, dated May 31, 2016, 2 pages.
Australian examination report in patent application No. 2016202801, dated Jun. 20, 2016, 2 pages.
Canadian Examination Report in patent application No. 2655839, dated Oct. 4, 2013, 2 pages.
Canadian Examination Report in patent application No. 2890556, dated Jan. 27, 2016, 3 pages.

(56) References Cited

OTHER PUBLICATIONS

Chinese Examination Report in patent application No. 2007800266164, dated Feb. 17, 2011, 5 pages.
Chinese Examination Report in patent application No. 201080028029.0, dated Mar. 27, 2014, 16 pages.
Chinese Second Office Action in patent application No. 201080028029.0, dated Jan. 19, 2015, 16 pages.
Chinese Examination Report in patent application No. 201080028029.0, dated Sep. 14, 2015, 3 pages.
Chinese Examination Report in patent application No. 201080061122.1, dated Jul. 17, 2015, 10 pages.
Chinese Examination Report in patent application No. 201080061122.1, dated Sep. 3, 2015, 10 pages.
Chinese First Office Action in patent application No. 201210080441.8, dated Mar. 24, 2014, 4 pages.
Chinese Second Office Action for Chinese Patent Application No. 201210080441.8 dated Dec. 1, 2014 in 11 pages (with English translation).
European Extended Search Report; dated Apr. 2, 2014; Application No. 09819444.2; 8 pages.
European Examination Report in patent application No. 07808683.2, dated Jul. 8, 2015, 8 pages.
European Extended Search Report in patent application No. 10774623.2, dated Sep. 8, 2015, 7 pages.
European Extended Search Report in patent application No. 10830251.4, dated Sep. 4, 2015, 7 pages.
Great Britain Combined Search and Examination Report in patent application No. GB1406401.8, dated May 7, 2014, 4 pages.
Great Britain Combined Search and Examination Report in patent application No. GB1406402.6, dated May 7, 2014, 6 pages.
Great Britain Examination Report in patent application No. GB1119385.1, dated May 9, 2013, 4 pages.
Great Britain Search and Examination Report, in patent application No. GB1210075.6, dated Mar. 14, 2013, 2 pages.
International Search Report for application No. PCT/NZ2005/000062 dated May 27, 2005.
International Search Report for International application No. PCT/NZ2007/000185, dated Oct. 31, 2007, in 3 pages.
International Search Report, PCT/NZ2009/000072, dated Jul. 28, 2009, 4 pages.
International Search Report, International application No. PCT/NZ2009/000219, dated Feb. 2, 2010, 3 pages.
International Preliminary Report on Patentability (IPRP), International application No. PCT/NZ2009/000219, dated Apr. 12, 2011, 9 pages.
International Search Report, PCT/NZ2010/000229, dated Mar. 18, 2011, 8 pages.
International Preliminary Report on Patentability and Written Opinion of the ISA, International application No. PCT/NZ2010/000229, dated May 22, 2012, 14 pages.
Written Opinion of the International Searching Authority, PCT/NZ2010/000229, dated Mar. 18, 2011, 13 pages.
International Search Report, application No. PCT/NZ2013/000138, dated Nov. 1, 2013, 7 pages.
Written Opinion of the International Searching Authority, PCT/NZ2013/000139, dated Nov. 1, 2013.
Japanese Examination Report in patent application No. 2012-510418, dated Feb. 10, 2014, 4 pages.
Japanese Examination Report in patent application No. 2012-538784, dated Aug. 25, 2014, 3 pages.
Japanese Examination Report in patent application No. 2012-538784, dated Aug. 5, 2015, 8 pages.
Japanese Examination Report in patent application No. 2015-098324, dated Jul. 22, 2015, 8 pages.
Petition for Inter Partes Review of U.S. Pat. No. 8.479,741 Pursuant to 35 U.S.C. §§ 311-19, 37 C.F.R. § 42, IPR2016-01714, dated Sep. 7, 2016.
Declaration of Dr. John Izuchukwu, Ph.D., P.E., U.S. Pat. No. 8,443,807, IPR Nos. 2016-1726 & 2016-1734, dated Sep. 7, 2016.

Declaration of Dr. John Izuchukwu, Ph.D., P.E., U.S. Pat. No. 8,479,741, IPR Nos. 2016-1714 & 2016-1718, dated Sep. 7, 2016.
Petition for Inter Partes Review of U.S. Pat. No. 8,479,741 Pursuant to 35 U.S.C. §§ 311-19, 37 C.F.R. § 42, IPR2016-01718, dated Sep. 7, 2016.
Petition for Inter Partes Review of U.S. Pat. No. 8,443,807 Pursuant to 35 U.S.C. §§ 311-19, 37 C.F.R. § 42, IPR2016-01726, dated Sep. 7, 2016.
Petition for Inter Partes Review of U.S. Pat. No. 8.443,807 Pursuant to 35 U.S.C. §§ 311-19, 37 C.F.R. § 42, IPR2016-01734, dated Sep. 7, 2016.
File History of U.S. Pat. No. 8,479,741 to McAuley et al., published Oct. 1, 2009.
File History of U.S. Pat. No. 8,443,807 to McAuley et al., published Jan. 7, 2010.
Patent Owner's Complaint for *Fisher & Paykel Healthcare Ltd.* v. *ResMed Corp.*, Case No. 2:16-cv-06099-R-AJW (C.D. Cal.), dated Aug. 15, 2016.
Patent Owner's Notice of Voluntary Dismissal Without Prejudice for *Fisher & Paykel Healthcare Ltd.* v. *ResMed Corp.*, Case No. 2:16-cv-06099-R-AJW (C.D. Cal.), dated Aug. 16, 2016.
Patent Owner's Complaint for *Fisher & Paykel Healthcare Ltd.* v. *ResMed Corp.*, Case No. 3:16-cv-02068-GPC-WVG (S.D. Cal.), dated Aug. 16, 2016.
Petitioners' Complaint for *ResMed Inc., et al.* v. *Fisher & Paykel Healthcare Corp. Ltd., et al.*, Case No. 3:16-cv-02072-JAH-MDD (S.D. Cal.), dated Aug. 16, 2016.
Petitioners' Notice of Voluntary Dismissal Without Prejudice for *ResMed Inc., et al.* v. *Fisher & Paykel Healthcare Corp. Ltd., et al.*, Case No. 3:16-cv-02072-JAH-MDD (S.D. Cal.), dated Aug. 18, 2016.
Statutory Declaration made by Alistair Edwin McAuley, Apr. 9, 2015, in the matter of an Opposition by Fisher & Paykel Healthcare Limited of Australian patent application 2009221630 in the name of ResMed Limited.
Resmed Mirage Swift™ II Nasal Pillows System product page (http://www.resmed.com/en-us/products/masks/miraqe_swift_II_nasal_pillows._system/Miraqe-Swift-II-Nasal-Pillows-System.html?menu=products); archived Jul. 21, 2008, 2 pp.
Resmed Mirage Swift™ II user brochure (http://www.resmed.com/en us/products/masks/mirage-swift_II_nasal_pillows_system/documents/mirage-swift-ii-np-brochure-patient-english-usa.pdf) copyright 2007, 4 pp.
ResMed Mirage Swift II Fitting guide (http://www:resmed.com/en-us/products/masks/miraqe_swift_II_nasal_pillows_system/documents/mirage-swift_ii_np-fitting_English.pdf) copyright 2006, 2 pp.
ResMed Mirage Swift II comparison to older Swift patient interface (http://www.resmed.com/en-us/products/masks/mirage_swift_II_nasal_pillows_system/documents/mirage-swift-ii-np-comparison-guide.pdf, 2007, 6 pp.
ResMed Mirage Swift II user guide (http://www.resmed.com/en-us/products/service_and_support/documents/60893rl_mirage_swiftII_nasal_userglide_us_multi.pdf) copyright 2006, 1 p.
ResMed Mirage Swift II component card (http://www.resmed.com/en-us/products/masks/mirage_swift_II_nasal_pillows_system/documents/mirage-swift-ii-np-cc-usa.pdf); copyright 2006, 2 pp.
Resmed Swift™ LT Nasal Pillows System, product page, (http://www.resmed.com/en-us/products/masks/mirage_swift_II_nasal_pillows_system/Mirage-Swift-II-Nasal_Pillows-System.html?menu=products), Jul. 3, 2008, 2 pp.
Resmed Swift LT user brochure, (http://www.resmed.com/en-us/products/masks/mirage_swift_II_nasal_pillows_system/documents/mirage-swift-ii-np-brochure-patient-english-usa.pdf), copyright 2008, 4 pp.
Resmed Swift™ LT component card (http://www.resmed.com/en-us/assets/documents/product/swift_It/components_card/1012463_swift-It_components-card_usa_eng.pdf) copyright 2008, 46 pp.
Resmed Swift™ LT fitting guide, (http://www.resmed.com/en-us/assets/documents/product/swift-II/clinical_fact_sheet/1012406 swift-ii_fact-sheet_usa_eng.pdf), 2008, 2 pp.
Resmed Swift™ LT fact sheet (http://www.resmcd.com/en-us/assets/documents/product/swift-It/clinical_fact_sheet/1012406 swiftIt_fact-sheet_usa_eng.pdf, copyright 2008, 4 pp.

(56) References Cited

OTHER PUBLICATIONS

Resmed Swift™ LT image gallery (http://www.resmed.com/en-us/products/masks/swift_It_nasal_pillows_system/imagegallery.html?menu=products, Apr. 25, 2008, 2 pp.
Resmed Swift™ LT interactive fitting guide—screenshot from troubleshooting part (http://www.resmed.com/enus/assets/multimedia/product/swift-It/flash/swift-It-fitting-eng.swf), Jul. 3, 2008, 2 pp.
Puritan Bennett Breeze® SleepGear® CPAP Interface, product page (http:/puritanbennett.com/prod/product.aspx?id=233); archived Oct. 19, 2007, 2 pp.
Puritan Bennett Breeze® SleepGear® User's Guide (http://puritanbennett.com/_catalog/pdf/dfu/107598a00[I].pdf); copyright 2007, 18 pp.
Puritan Bennett Breeze® SleepGear® sales sheet (http://www.puritanbennett.com/_Catalog/PDF/Product/BreezeSleepGear.pdf) copyright 2016, 7 PP.
Puritan Bennett mask coding matrix (http://www.puritanbennett.com/_Catalog/PDF/Product/BreezeSlpGear(ST03700).pdf) copyright 2006, 3 pp.
Puritan Bennett Breeze fitting guide (http://www.puritanbennett.com/_Catalog/PDF/Product/BreezeFittingPoster.pdf, Oct. 19, 2007, 1 p.
Respironics Optilife Pillows mask product page (http://optilife.respironics.com:80/); archived Nov. 21, 2007, 2 pp.
Respironics Optilife Pillows mask part numbers page (http://optilife.respironics.com:80/Parts.aspx); archived Nov. 23, 2007, 4 pp.
Respironics Optilife Pillows mask FAQ (http://optilife.respironics.com:80/fags.aspx); archived Nov. 23, 2007, 6 pp.
Respironics Optilife Pillows mask feature page (http://optilife.respironics.com:80/features.aspx); archived Nov. 23, 2007, 4 pp.
Respironics Optilife Pillows mask fitting guide screen shot (http://optilife.respironics.com:80/fittingGuide.aspx); archived Aug. 7, 2008, 1 p.
Respironics Optilife Pillows mask adjustment video screenshots, https://www.youtube.com/watch?v=shjcNmvvcBA); uploaded Aug. 3, 2008, 2 pp.
Puritan Bennett Breeze description; copyright 2000 by Mallinckrodt Inc., 4 pp.
Fisher & Paykel Opus product page, archived Sep. 3, 2009, 2 pp.
Fisher & Paykel Opus patient interface product photographs, Jul. 2007, 6 pp.
Photographs of Opus 360 nasal pillows mask patient instructions RevB, Jul. 2007, 4 pp.
Respironics Optilife brochure detailing updates; copyright 2008; dated Mar. 26, 2008, 3 pp.
Fisher & Paykel Opus product page, archived Sep. 7, 2009, 2 pp.
Fisher & Paykel Opus "Off-the-lips" pillows explanation page, archived Aug. 23, 2009, 2 pp.
Fisher & Paykel Opus "Off-the-lips" patient interface brochure, archived Oct. 14, 2009, 6 pp.
Fisher & Paykel Opus user-guide, archived Nov. 17, 2009, 2 pp.
Fisher & Paykel Healthcare, FlexiFit® 431 Full Face Mask instructions, 2010, 4 pp.
Fisher & Paykel Healthcare, Interface Solutions Product Profile, 2006, 12 pp.
Australian Examination Report No. 1, in patent application No. AU 2013300237, dated Jun. 8, 2017, in 4 pages.
Australian Examination Report in patent application No. 2016238904 dated May 4, 2018, 5 pages.
Australian Examination Report in patent application No. 2010241390, dated Sep. 28, 2016, 4 pages.
Australian Examination Report in patent application No. 2016204384, dated Aug. 5, 2016, 2 pages.
Australian examination report in patent application No. 2017200991, dated Oct. 13, 2017, 3 pages.
Australian examination report in patent application No. 2017201021, dated Apr. 7, 2017, 6 pages.
Australian examination report in patent application No. 2018202409, dated Jan. 21, 2019, 4 pages.
Australian examination report in patent application No. 2018201975, dated Mar. 30, 2019, 4 pages.
Australian examination report in patent application No. 2018217307, dated Mar. 4, 2019, 4 pages.
Australian examination report in patent application No. 2018236891, dated Jun. 25, 2019, 3 pages.
Australian Examination Report No. 2 for patent application No. 2018217307, dated Mar. 3, 2020, 4 pp.
Brazilian office action dated Jul. 11, 2019 in patent application No. BR11201211420-4.
Canadian Examination Report in patent application No. 2780310, dated Jul. 26, 2016, 4 pages.
Canadian Examination Report in patent application No. 2780310, dated Jan. 25, 2018 4 pages.
Canadian Examination Report in patent application No. 2780310, dated Oct. 9, 2018, 3 pp.
Canadian Examination Report in patent application No. 2890556, dated Nov. 28, 2016, 4 pages.
Canadian Examination Report in patent application No. 2918167, dated Oct. 3, 2016, 4 pages.
Canadian Examination Report in patent application No. 2998247, dated Jan. 8, 2019, 4 pages.
Canadian Examination Report in patent application No. 3010066, dated May 3, 2019, 4 pages.
Canadian Examination Report in patent application No. 3010066, dated Dec. 19, 2019, 4 pages.
Canadian Examination Report in patent application No. 2880749, dated May 16, 2019, 5 pages.
Canadian Examination Report in patent application No. 3017161, dated Aug. 21, 2019, 3 pp.
Canadian Examination Report for patent application No. 2880749, dated Feb. 28, 2020, 4 pp.
Chinese Office Action in patent application No. 201610116121.1, dated Sep. 28, 2017, 5 pages.
Chinese Third Office Action in patent application No. 201610116121.1, dated Apr. 28, 2019, 16 pages.
Chinese Fourth Office Action in patent application No. 201610116121.1, dated Sep. 30, 2019, 12 pages.
Chinese Third Office Action in patent application No. 201080061122.1, dated Apr. 1, 2016, 5 pages.
Chinese Examination Report in patent application No. 201610114706.X, dated Jul. 30, 2018, 9 pp., with translation.
Chinese Second Examination Report in patent application No. 201610114706.X, dated Apr. 24, 2019 8 pp., with translation.
Chinese Third Examination Report in patent application No. 201610114706.X, dated Jan. 16, 2020, with translation.
Chinese Examination Report dated Feb. 22, 2019 in patent application No. 201611251618.0.
Chinese First Office Action in patent application No. 201710824612.6, dated Sep. 30, 2019, 25 pp.
European Examination Report in patent application No. 07808683.2, dated May 9, 2018, 3 pages.
European Search Report and Written Opinion dated May 12, 2016 in patent application No. 09746823.5; 11 pages.
European Summons to Attend Oral Proceedings and Written Opinion dated Dec. 13, 2017 in patent application No. 09746823.5; 7 pages.
European Examination Report in patent application No. 09746823.5, dated Apr. 3, 2017, 2 pages.
European Examination Report, European Application 13828380.9, dated Apr. 7, 2017, 7 pp.
European Examination Report, European Application 13828380.9, dated Jul. 27, 2018, 8 pp.
European Examination Report, European Application 13828380.9, dated Mar. 3, 2020, 8 pp.
European extended search report dated Jul. 23, 2018 in patent application No. 18163847.9, 7 pp.
European examination report dated Sep. 5, 2019 in patent application No. 18163847.9, 5 pp.
European extended search report dated Sep. 21, 2018 in patent application No. 18178220.2, 7 pp.
European extended search report dated Oct. 31, 2018 in patent application No. 18171619.2, 9 pp.

(56) References Cited

OTHER PUBLICATIONS

European Extended Search Report in patent application No. 17179765.7, dated Dec. 11, 2017.
European Extended Search Report dated Feb. 14, 2019 in patent application No. 18195537.8.
European Examination Report dated Mar. 16, 2020 in patent application No. 18195537.8.
European Search Report in patent application No. 11830981.4, dated Aug. 24, 2015, 6 pages.
European Search Report in patent application No. 191976761.1, dated Mar. 3, 2020, 10 pages.
Great Britain Combined Search and Examination Report in patent application No. GB1719334.3, dated Nov. 30, 2017, in 9 pages.
Great Britain examination report dated May 30, 2018 in patent application No. GB1719334.3, 4 pp.
Great Britain examination report dated Jul. 20, 2018 in patent application No. GB1719334.3, 3 pp.
Great Britain combined search and examination report dated May 11, 2018 in patent application No. GB 1805606.9, 7 pp.
Great Britain examination report dated Jul. 5, 2018 in patent application No. GB1805606.9, 3 pp.
Great Britain examination report dated May 11, 2018 in patent application No. GB1803255.7, 7 pp.
Great Britain examination report dated May 11, 2018 in patent application No. GB1805605.1, 7 pp.
Great Britain examination report in patent application No. GB1501499.6, dated Jun. 1, 2017, in 8 pages.
Great Britain Combined Search and Examination Report under Section 18(3), Application No. GB1501499.6, dated Oct. 12, 2017, in 4 pages.
Indian Examination Report dated Mar. 14, 2019 in patent application No. 1431/KOLNP/2012.
Indian Examination Report dated Mar. 14, 2019 in patent application No. 8767/CHENP/2011.
International Search Report, PCT/NZ2011/000211, dated Feb. 17, 2012, 4 pages.
Written Opinion, PCT/NZ2011/000211, dated Feb. 17, 2012, 7 pages.
International Search Report for International application No. PCT/NZ2014/000021, filed Feb. 21, 2014.
Indian Office Action in Patent Application No. 5250/KOLNP/2008, dated May 23, 2017, 8 pages.
Japanese Examination Report in patent application No. 2012-538784, dated Jul. 25, 2016, 2 pages.
Japanese Examination Report in patent application No. 2017-040092, dated Feb. 5, 2018.
Japanese Official Action dated Sep. 3, 2018 in patent application No. 2017-238259.
Japanese examination report in patent application No. 2015-526496, dated Apr. 17, 2017, in 13 pages.
Japanese Examination Report in patent application No. 2015-526496, dated Feb. 28, 2018, 2 pp.
Japanese Decision for Final Rejection dated Jul. 1, 2019 in patent application No. 2017-238259, 2 pp.
Japanese office action dated Sep. 1, 2019 in patent application No. 2018-188040.
Japanese Pretrial Examination Report dated Jan. 7, 2020 in patent application No. 2017-238259.
U.S. Appl. No. 61/064,406, 34 pages, provided by USPTO on Feb. 23, 2009.
U.S. Appl. No. 61/071,893, 43 pages, provided by USPTO on Feb. 23, 2009.
U.S. Appl. No. 61/136,617, 82 pages, provided by USPTO on Feb. 23, 2009.
Patent Owner Preliminary Response to Petition for Inter Partes Review of U.S. Pat. No. 8,479,741, IPR2016-01714, filed Dec. 14, 2016.
Decision Denying Institution of Inter Partes Review of U.S. Pat. No. 8,479,741 Pursuant to 37 C.F.R. §42.108, IPR2016-01714, entered Mar. 10, 2017.
Patent Owner Preliminary Response to Petition for Inter Partes Review of U.S. Pat. No. 8,479,741, IPR2016-01718, filed Dec. 16, 2016.
Decision Denying Institution of Inter Partes Review of U.S. Pat. No. 8,479,741 Pursuant to 37 C.F.R. § 42.108, IPR2016-01718, entered Mar. 13, 2017.
Patent Owner Preliminary Response to Petition for Inter Partes Review of U.S. Pat. No. 8,443,807, IPR2016-01726, filed Dec. 13, 2016.
Decision Denying Institution of Inter Partes Review of U.S. Pat. No. 8,443,807 Pursuant to 37 C.F.R. § 42.108, IPR2016-01726, entered Mar. 6, 2017.
Patent Owner Preliminary Response to Petition for Inter Partes Review of U.S. Pat. No. 8,443,807, IPR2016-01734, filed Dec. 22, 2016.
Decision Denying Institution of Inter Partes Review of U.S. Pat. No. 8,443,807 Pursuant to 37 C.F.R. § 42.108, IPR2016-01734, entered Mar. 13, 2017.
Statutory Declaration made by Alistair Edwin McAuley, Apr. 14, 2015, in the matter of an Opposition by Fisher & Paykel Healthcare Limited of Australian patent application 2009221630 in the name of ResMed Limited.
Statutory Declaration made by Alistair Edwin McAuley, Apr. 17, 2015, in the matter of an Opposition by Fisher & Paykel Healthcare Limited of Australian patent application 2009221630 in the name of ResMed Limited.
Statutory Declaration made by Alistair Edwin McAuley, Sep. 16, 2015, in the matter of an Opposition by Fisher & Paykel Healthcare Limited of Australian patent application 2009221630 in the name of ResMed Limited.
First Affidavit of Alistair Edwin McAuley, Dec. 5, 2016, in the matter of *Fisher and Paykel Healthcare Limited v. ResMed Limited* filed in the Federal Court of Australia.
Second Affidavit of Alistair Edwin McAuley, Dec. 21, 2016, in the matter of *Fisher and Paykel Healthcare Limited v. ResMed Limited* filed in the Federal Court of Australia.
Third Affidavit of Alistair Edwin McAuley, Jan. 31, 2017, in the matter of *Fisher and Paykel Healthcare Limited v. ResMed Limited* filed in the Federal Court of Australia, 284 pp.
Declaration of Anthony Michael Ging in IPR 2019-000172, IPR 2019-000173, IPR 2019-000177, IPR 2019-000178, dated Nov. 8, 2018, 329 pp.
McGraw-Hill Dictionary of Scientific and Technical Terms, Sixth Edition, 2003, Tube, p. 2200.
Claim Chart for AirFit P10, U.S. Pat. No. 9,333,315, dated Nov. 7, 2018, 3 pp.
Scheduling Order dated Jul. 16, 2019 in IPR2019-00180, 12 pp.
Decision to Institute dated Jul. 16, 2019 in IPR2019-00180, 34 pp.
Decision Denying Institute of Inter Partes Review dated Jul. 16, 2019 in IRP2019-00179, 32 pp.
Australian examination report in patent application No. 2018236891, dated Jun. 9, 2020, 3 pages.
Australian Examination Report No. 1 in patent application No. 2019280016, dated Jul. 22, 2020.
Brazilian office action dated Aug. 28, 2020 in patent application No. PI1012207-9.
Chinese Fourth Examination Report in patent application No. 201610114706.X, dated Aug. 28, 2020, with translation.
Chinese Second Office Action in patent application No. 201710824612.6, dated May 25, 2020.
European examination report dated Jun. 16, 2020 in patent application No. 18163847.9, 5 pp.
European Extended Search Report dated Jul. 7, 2020 in patent application No. 19217524.8, 13 pp.
German examination report dated Aug. 31, 2020 in patent application No. 11 2010 011 994.0, 18 pp.
Canadian Examination Report in patent application No. 3010066, dated Nov. 9, 2020, 3 pages.
Canadian Examination Report in patent application No. 3017161, dated Nov. 25, 2020, 4 pp.
Canadian Examination Report for patent application No. 2880749, dated Oct. 5, 2020, 4 pp.

(56) References Cited

OTHER PUBLICATIONS

European Examination Report dated Jan. 13, 2021 in patent application No. 18195537.8.
European Examination Report in patent application No. 191976761.1, dated Dec. 11, 2020, 6 pages.
European Extended Search Report dated Oct. 6, 2020 in patent application No. 20184447.9, 9 pp.
Japanese Notification of Reason for Rejection dated Nov. 2, 2020 in patent application No. 2017-238259.

* cited by examiner

BREATHING ASSISTANCE APPARATUS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

This application is a continuation application of U.S. patent application Ser. No. 15/372,293, filed Dec. 7, 2016 which is a continuation application of U.S. patent application Ser. No. 15/088,628, filed Apr. 1, 2016, which is a continuation application of U.S. patent application Ser. No. 14/887,212, filed Oct. 19, 2015, which is a continuation of U.S. patent application Ser. No. 14/812,167, filed Jul. 29, 2015, which is a continuation of U.S. patent application Ser. No. 12/633,135, filed Dec. 8, 2009, which is a continuation application of U.S. patent application Ser. No. 12/307,993 filed on Jun. 17, 2009, which is a 371 filing of PCT/NZ2007/000185 filed on Jul. 13, 2007 and published in English as WO 2008/007985 on Jan. 17, 2008, which claims priority from New Zealand Application No. 548575 filed on Jul. 14, 2006 and New Zealand Application No. 551103 filed on Nov. 6, 2006. All of these applications are hereby incorporated by reference in their entirety.

BACKGROUND OF THE INVENTION

Field of the Invention

The present invention relates to apparatus for treating sleep apnoea. More specifically, the present invention provides a nasal interface for the supply of respiratory gases, but most particularly positive pressure gases.

Description of the Related Art

In the art of respiration devices, a variety of respiratory masks which cover the nose and/or mouth of a human user in order to provide a continuous seal around the nasal and/or oral areas of the face are well known. Masks that provide gas at positive pressure within the mask for consumption by the user are also well known. The uses for such masks range from high altitude breathing (i.e., aviation applications) to mining and fire fighting applications, to various medical diagnostic and therapeutic applications.

Obstructive Sleep Apnoea (OSA) is a sleep disorder that affects up to at least 5% of the population in which muscles that normally hold the airway open relax and ultimately collapse, sealing the airway. The sleep pattern of an OSA sufferer is characterised by repeated sequences of snoring, breathing difficulty, lack of breathing, waking with a start and then returning to sleep. Often the sufferer is unaware of this pattern occurring. Sufferers of OSA usually experience daytime drowsiness and irritability due to a lack of good continuous sleep.

In an effort to treat OSA sufferers, a technique known as Continuous Positive Airway Pressure (CPAP) was devised. A CPAP device consists of a gases supply (or blower) with a conduit connected to supply pressurised gases to a patient, usually through a nasal mask. The pressurised air supplied to the patient effectively assists the muscles to keep the patient's airway open, eliminating the typical OSA sleep pattern.

The procedure for administering CPAP treatment has been well documented in both the technical and patent literature.

Briefly stated, CPAP treatment acts as a pneumatic splint of the airway by the provision of a positive pressure, usually in the range 4 to 20 cm $H_2O$. The air is supplied to the airway by a motor driven blower whose outlet passes via an air delivery hose to a nose, full face, nose and mouth, or oral mask that is sealingly engaged to a patient's face, preferably by means of a harness or other headgear. An exhaust port is usually also provided in the delivery tube proximate to the mask or on the mask itself. More sophisticated forms of positive airway pressure devices, such as bi-level devices and auto-titrating devices, are described in U.S. Pat. No. 5,148,802 of Respironics, Inc. and U.S. Pat. No. 5,245,995 of Rescare Limited, respectively.

One requisite of respiratory masks has been that they provide an effective seal against the user's face to prevent leakage of the gas being supplied. Commonly, in prior mask configurations, a good mask-to-face seal has been attained in many instances only with considerable discomfort for the user. A common complaint of a user of CPAP therapy is pressure sores caused by the mask about the nose and face and in particular in the nasal bridge region of the user. This problem is most crucial in those applications, especially medical applications, which require the user to wear such a mask continuously for hours or perhaps even days. In such situations, the user will not tolerate the mask for long durations and optimum therapeutic or diagnostic objectives thus will not be achieved, or will be achieved with great difficulty and considerable user discomfort.

U.S. Pat. No. 5,477,852 of Airways Ltd, Inc. discloses a nasal positive airway pressure device that has a pair of nasal members each having a cannula tip to be inserted into the nares of the patient. Each cannula is tapered from a substantially circular cross section outside the patient's nostril to a substantially oval cross section at the tip inserted into the nostril. An inflatable cuff surrounds each cannula with the interior space of the cuff communicating with the lumen of the cannula through at least one aperture in the sidewall of the cannula. The nasal members are connected to one or more flexible hoses that; in turn, are connected to a source of positive air pressure. In use, positive air pressure is supplied to each cannula tip through the air hoses and nasal members. The positive air pressure inflates the cuffs to hold the nasal members in place and to effect treatment. The nasal device of U.S. Pat. No. 5,477,852 is attached to headgear that is located about a patient's head. This headgear could be considered by many patients as cumbersome and uncomfortable.

Conventional nasal masks used for administrating CPAP treatment are also considered uncomfortable and cumbersome, and prior art nasal masks can be noisy due to air leaks. These disadvantages in many cases are a formidable obstacle to patient acceptance of such treatment. Therefore, a substantial number of patients either cannot tolerate treatment or choose to forego treatment. It is believed a number of such patients might benefit from a nasal positive airway pressure apparatus that is more convenient to use and comfortable to wear, thereby resulting in increased treatment compliance.

Innomed Technologies, Inc. manufactures a nasal cannula device called the NASALAIRE™. In this device air or oxygen travels down a wide bore conduit to nasal cannula. The NASALAIRE™ creates a physical seal between the flares and itself, and relies on the absence of leaks around the cannula and the nares to deliver pressure supplied by a continuous positive airway pressure (CPAP) blower to the airway of the wearer.

U.S. Pat. No. 6,119,694 of Respironics Ga., Inc discloses a nasal mask having a nare seal and lateral support members to support the mask.

WO2004/073778 of ResMed Limited discloses a nasal mask including a frame where headgear is provided with rigid sections that extend to the nasal mask.

WO04/041341 of ResMed Limited discloses headgear for a patient mask that includes a sewn on rigid section to the back area of headgear straps to provide rigidity to the straps.

U.S. Pat. No. 6,907,882 of ResMed Limited discloses a nasal mask and headgear that is attachable to the frame of the nasal mask. The headgear straps have rigid sections integral with the releasable connectors that attach the headgear to the mask.

SUMMARY OF THE INVENTION

It is an object of the present invention to attempt to provide a patient interface that goes some way to overcoming the abovementioned disadvantages in the prior art or which will at least provide the industry with a useful choice.

In a first aspect the present invention consists in headgear for use with a respiratory mask comprising:

a continuous and substantially curved elongate member extending in use below a patient's nose, at least two headgear straps capable of attachment to the ends of said elongate member, and a mask attachment on said elongate member disposed to sit below or on one of said user's nose, mouth, upper lip and an inlet to the mask, said attachment capable of receiving said mask.

In a second aspect the present invention consists in a breathing assistance apparatus for use with delivery of respiratory gases to a user comprising:

a mask having a base and body, said body having two flexible nasal pillows that in use rest in a substantially sealed manner against said user's nares, a continuous and substantially curved elongate member extending in use below a patient's nose, at least two headgear straps capable of attachment to the ends of said elongate member, and a mask attachment on said elongate member disposed below said user's nose, said attachment capable of receiving said mask.

In a third aspect the present invention consists in a breathing assistance apparatus for use with delivery of respiratory gases to a user comprising:

a mask comprising a body and a cushion, said cushion substantially forming a seal with said patient's airways, headgear comprising substantially flexible, soft straps and a substantially continuous curved elongate member to which said mask is attached, said elongate member extending over said user's cheeks, and wherein said mask has an inlet extension tube and said curved elongate member is attached or rests beneath said inlet extension tube, anchoring said mask to said user's face in use.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

The invention consists in the foregoing and also envisages constructions of which the following gives examples.

BRIEF DESCRIPTION OF THE DRAWINGS

Preferred forms of the present invention will now be described with reference to the accompanying drawings.

DETAILED DESCRIPTION OF THE PREFERRED EMBODIMENT

The breathing assistance apparatus of the present invention including masks and headgear as described in the preferred embodiments of this invention can be used in respiratory care generally or with a ventilator. It is described below with reference to use in a humidified CPAP system.

Figure 1:
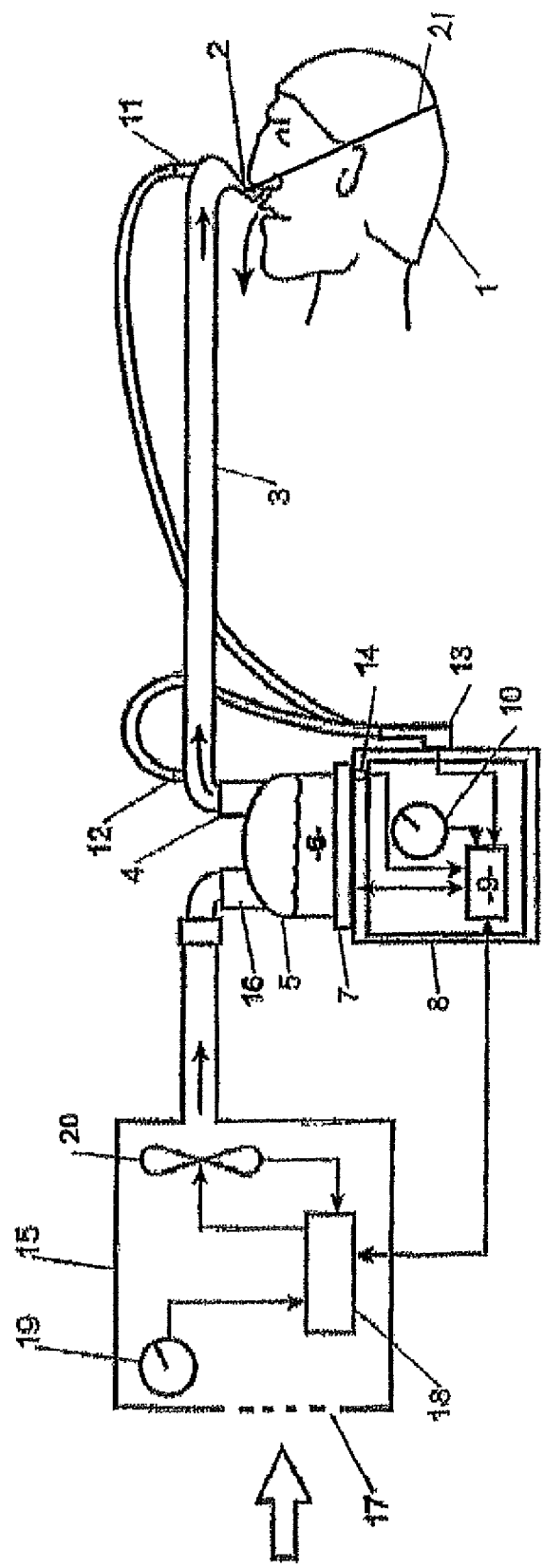
FIG. 1 is a block diagram of a humidified continuous positive airway pressure system as might be used in conjunction with the nasal mask of the present invention.
Figure 7:
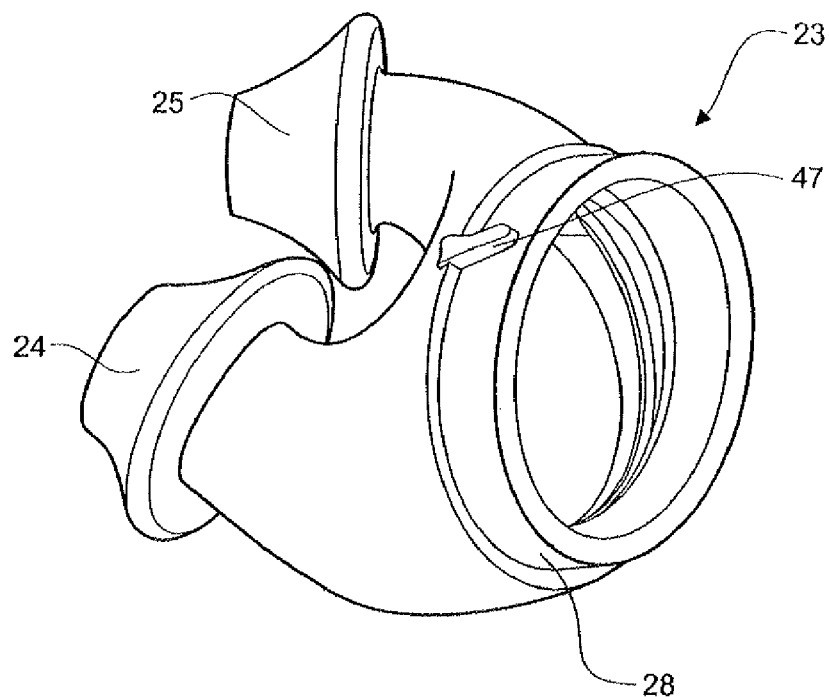
FIG. 7 is a perspective view of the body of FIG. 6.

A humidified Continuous Positive Airway Pressure (CPAP) system is shown in FIG. 1. A patient 1 is receiving humidified and pressurised gases through a patient interface 2 connected to a humidified gases transportation pathway or inspiratory conduit 3. Alternative delivery systems may also be used such as, VPAP (Variable Positive Airway Pressure) and BiPAP (Bi-level Positive Airway Pressure) or numerous other forms of respiratory therapy. A nasal mask 2 is illustrated in FIG. 7 but other masks such as oral, full face or nasal cannula may be used.

An inspiratory conduit 3 is connected to an outlet 4 of a humidification chamber 5 that contains a volume of water 6. The inspiratory conduit 3 may contain heating means or heater wires (not shown) that heat the walls of the conduit to reduce condensation of humidified gases within the conduit 3.

The humidification chamber 5 is preferably formed from a plastics material and preferably has a highly heat conductive base (for example an aluminium base) that is in direct contact with a heater plate 7 of humidifier 8. The humidifier 8 is provided with control means or an electronic controller 9 that may comprise a microprocessor based controller 9 executing computer software commands stored in associated memory.

The controller 9 preferably receives input from sources such as user input means or a dial 10 through which a user of the device may, for example, set a predetermined required value (preset value) of humidity or temperature of the gases supplied to patient 1. The controller 9 may also receive input from other sources, for example temperature and/or flow velocity sensors 11, 12, through a connector 13 and a heater plate temperature sensor 14. In response to the user set humidity or temperature value input via the dial 10 and the other inputs, the controller 9 determines when (or to what level) to energise the heater plate 7 to heat the water 6 within the humidification chamber 5. As the volume of the water 6 within the humidification chamber 5 is heated, water vapour begins to fill the volume of the chamber above the water's surface and is passed out of the humidification chamber 5 outlet 4 with the flow of gases (for example air) provided from a gases supply means or blower 15 that enters the chamber 5 through an inlet 16. Exhaled gases from the patient's mouth are passed directly to the ambient surroundings in FIG. 1.

The blower 15 is provided with variable pressure regulating means or variable speed fan 21 that draws air or other gases through a blower inlet 17. The speed of the variable speed fan 21 is controlled by an electronic controller 18 (or alternatively the function of the controller 18 may be carried out by the controller 9) in response to inputs from the controller 9 and a user set predetermined required value (preset value) of pressure or the fan speed via dial 19.

Figure 2:
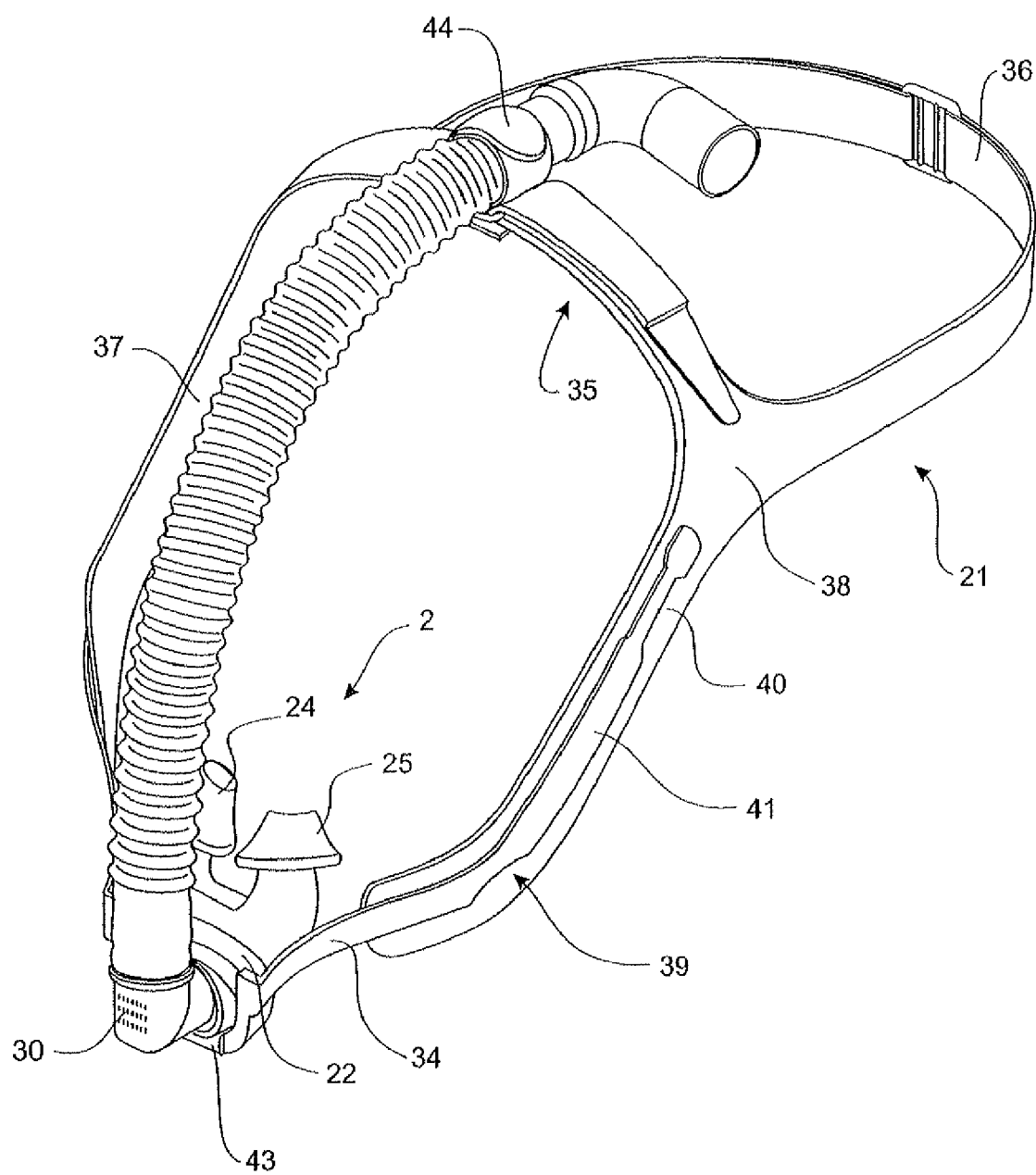
FIG. 2 is a perspective view of a first form of a patient interface that is nasal mask and headgear of the present invention.
Figure 3:
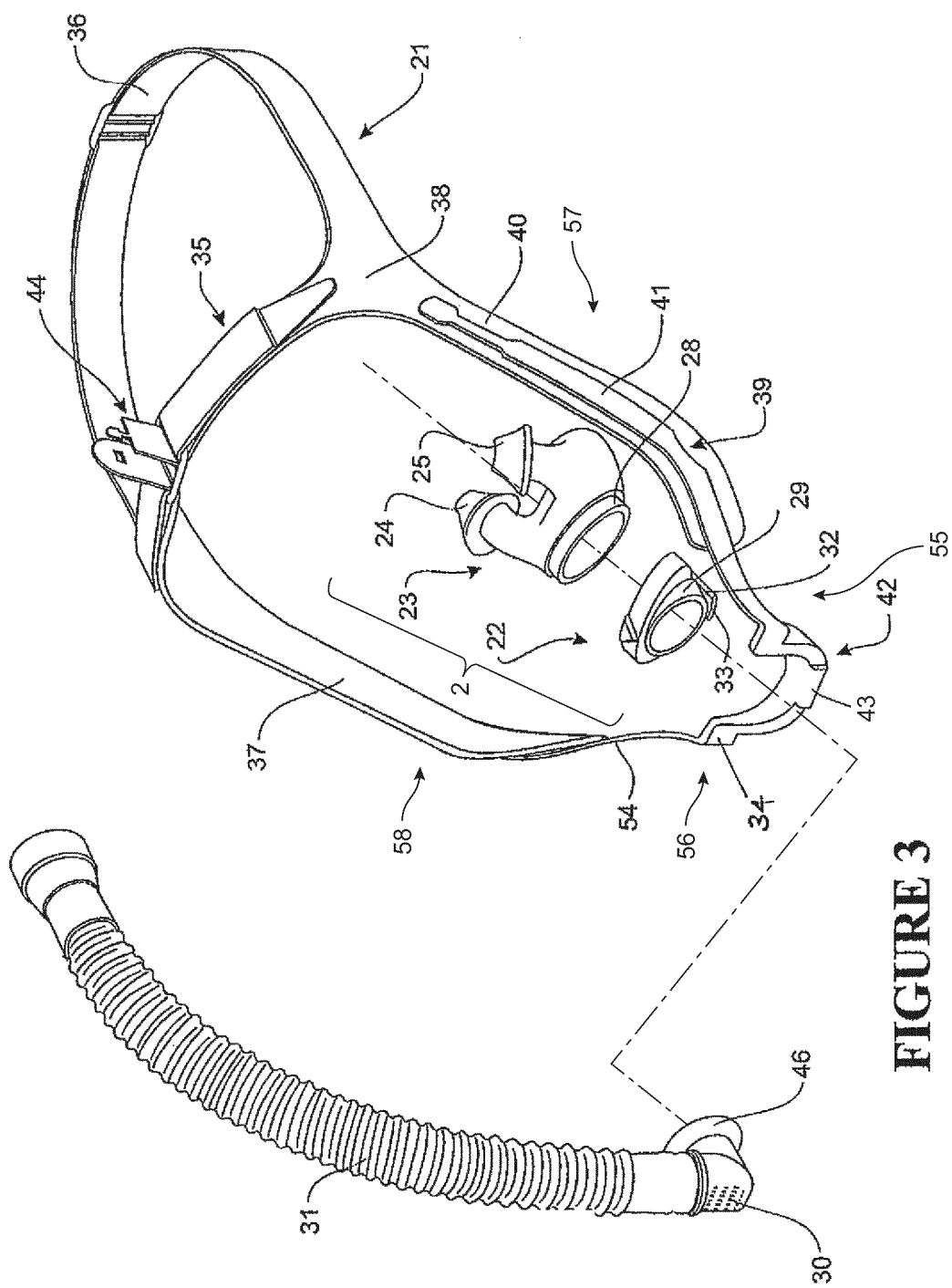
FIG. 3 is an exploded view of the nasal mask and headgear of FIG. 2.

FIGS. 2 and 3 show a first embodiment of a patient interface of the present invention. This patient interface is a nasal mask 2. The nasal mask 2 is comprised of a mask base 22 and body 23. The body 23 is substantially tubular with two nasal pillows 24, extending from it. The nasal pillows 24, 25 are preferably frustoconical in shape and in use rest against a patient's nares, to substantially seal the patient's nares. The body 23 has an external lip 28 that frictionally fits in a channel in the mask base 22.

Figure 6:
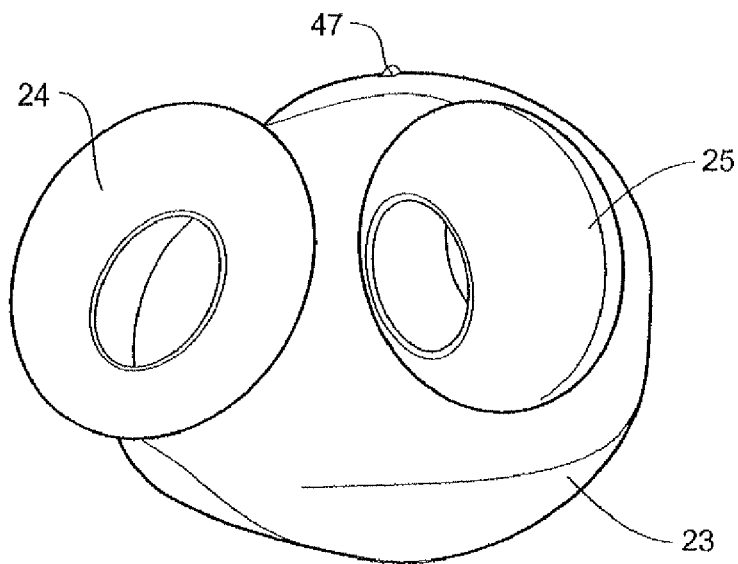
FIG. 6 is an end view of a body of the nasal mask and headgear of FIG. 2, particularly showing two nasal pillows.

The body 23 and nasal pillows 24, 25 of the nasal mask of the present invention are shown in further detail in FIGS. 6 and 7. The body and pillows are preferably integrally moulded in a substantially flexible plastics material. In the preferred form this material is silicone, but other appropriate materials, such as, rubber, thermoset elastomer or thermoplastic elastomer, such as Kraton™ may be used.

The nasal pillows 24, 25 are preferably an elliptical cone and as such are tubular and allow for a passage of gases to flow from the tubing 3 and through the mask body 23. The pillows 24, 25 are preferably angled toward one another and each have a preferably elliptical outlet 26, 27 that may be slightly offset from the centre of each pillow 24, 25, as shown in FIG. 6.

Figure 18:
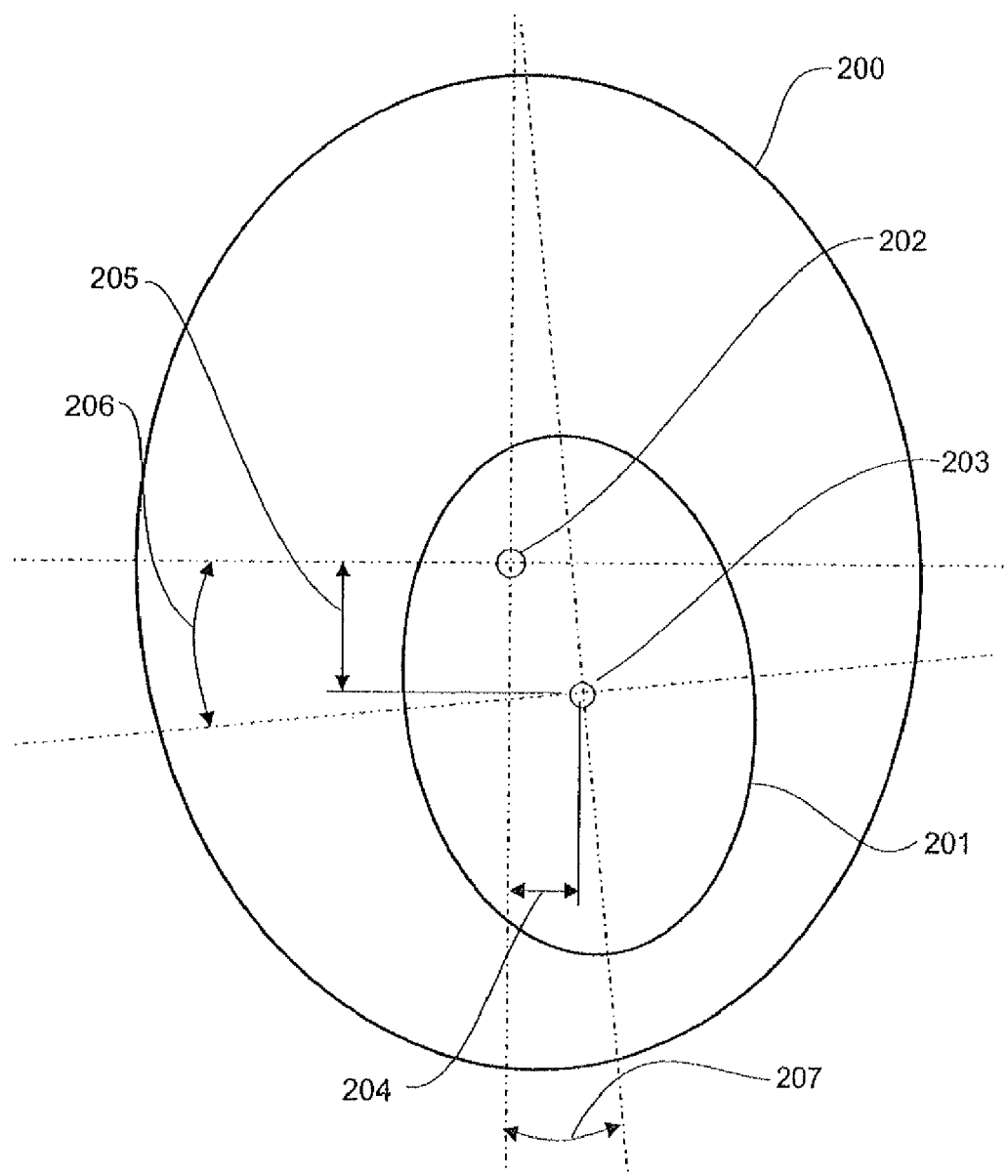
FIG. 18 is a front view of a nasal pillow of FIG. 6.
Figure 19B:
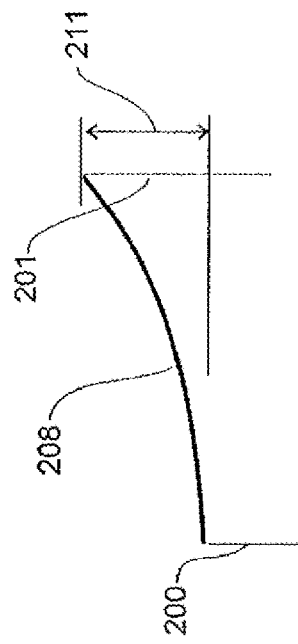
FIGS. 19b to 19d are graphs of the gradients of various nasal pillow connecting surfaces.
Figure 19C:
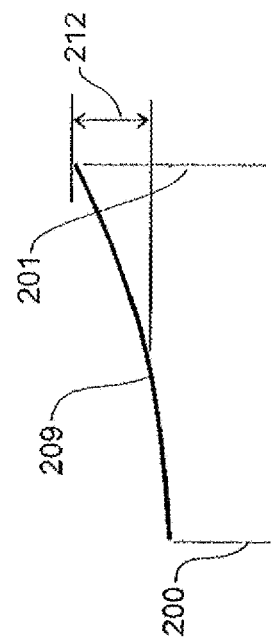
Figure 19D:
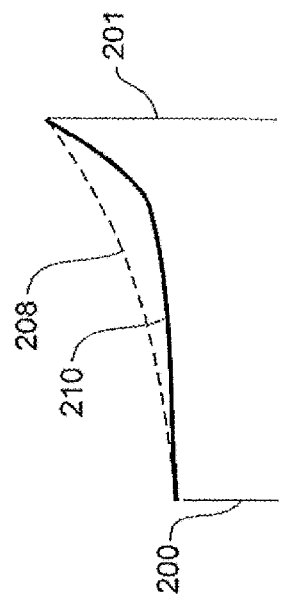
Figure 19A:
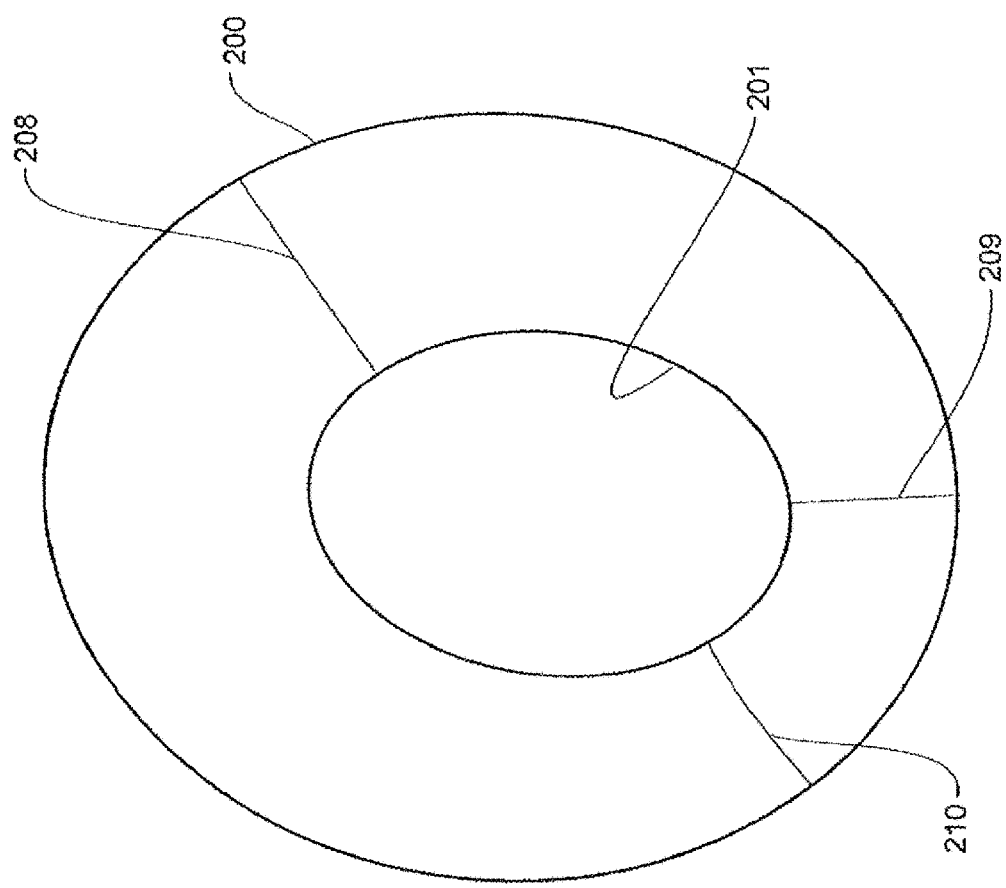
FIG. 19a is a front view of the nasal pillows of FIG. 6.

FIGS. 18 and 19a show a nasal pillow 24 with an offset outlet in more detail. The pillow 24 has an outer profile 200 and inner profile 201 with respective centre points 202, 203. The inner profile 201 (outlet of the nasal pillow 24) is offset inward, by a horizontal spacing 204 and vertical spacing 205. Meaning the outlet 201 of the nasal pillow is offset horizontally 204 towards the middle of the nose and vertically 205 towards the user's upper lip. Offsetting the outlet 201 downwards in this manner allows the outlet to be inserted into a user's nostril without the outer profile 200 pushing the user's upper lip. Offsetting the outlet 201 inwards allows the pillow to better seal on the septum of the user's nose in use.

The outlet 201 may also be angled compared to the outer profile 200. For example in FIG. 18, there is a horizontal angle difference between the outer profile 200 and outlet 201 shown as 206. A similar vertical angle difference between the outer profile 200 and outlet 201 is shown as 207.

With the outer profile and inner profile having different sections or offsets allows the gradient of the connecting surface between the profiles to be changeable. This is shown in the graphs of FIGS. 19b, 19c and 19d. The connecting surface between the inner 201 and outer 200 profiles can have differing gradients, 208, 209, 210. The different gradients 208, 209, 210 of the connecting surface are possible due to the difference in offset difference 211, 212 (horizontal, vertical or angled) between the inner 201 and outer 200 profiles.

There may also be a difference in the rate of change of the gradient (as illustrated in the difference between 208 and 210). This allows easier insertion of the pillow 24 into a user's nostrils due to more lead in and better sealing that may be achieved due to more ergonomic contouring of the connecting surface that contacts the user's nostril.

Referring back to FIG. 7, the external lip 28 on the mask body 23 is an area of reduced circumference around the tubular part of the body 23. A projection 47 may be provided on the lip 28 that fits with a corresponding recess or channel (discussed below) on the mask base 22 to ensure correct assembly of the nasal mask.

Figure 4:
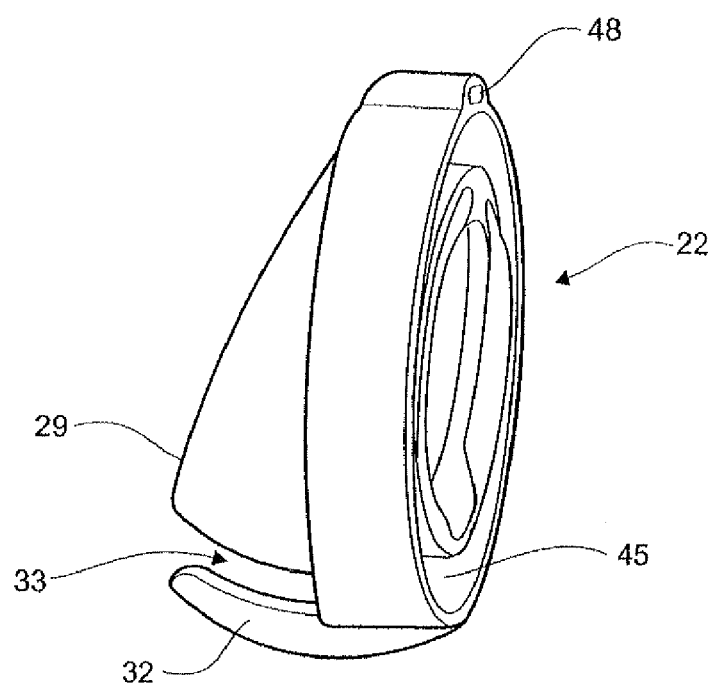
FIG. 4 is a side view of a mask base of the nasal mask and headgear of FIG. 2.
Figure 5:
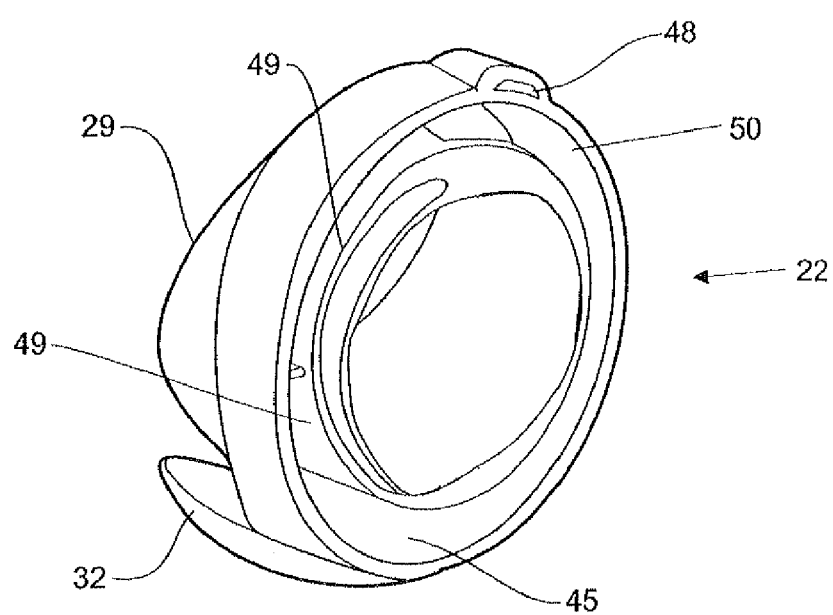
FIG. 5 is a perspective end view of the mask base of FIG. 4.

The mask base 22 is shown in further detail in FIGS. 4 and 5. The mask base 22 is a ring or sleeve type attachment. The base 22 is preferably made from a substantially hard (rigid) plastics material, such as polypropylene, polycarbonate or acetyl. However, other appropriate materials may be used. The base 22 has an internal circumferential recessed area or channel 45 on one side and a semi-tubular projection 29 on its other side. When assembling the mask body 23 to the mask base 22 the channel 45 receives the lip 28. These parts are maintained together by friction fit, however other types of fitting may be provided for, such as a snap or bump fitted part or the body may be over moulded to a clip that causes the fitting to the mask body 23. In this form the friction fitting of the lip 28 to the recessed area 45 is assisted by elongate projections 49 extending along the central part 50 of the mask base 22. The projection 47 on the mask body 23 allows for correct fitting or keying of the mask base to the mask body, such that when the lip 28 is fitted into the recessed area 45, the projection 47 enters the recess 48 formed in the mask base 22.

The semi-tubular projection 29 is curved in this embodiment such that a ball jointed connector end 46 such that a connector 30 can be fitted into it. The projection 29 forms a socket for the connector end 46 and the connector end can swivel within the socket. The connector 30 is attached to a tube 31 to allow for gases to be passed to the nasal mask 2. The tubing 31 may be attached to inspiratory conduit 3 or the tubing 31 may simply be the inspiratory conduit 3.

In alternative embodiments the projection 29 may not be semicircular but the inner surface of the base 22 may be curved and form a socket for receiving the connector end 46.

The base 22 has an extension or partial lip 32 extending beneath the semi-tubular projection (socket) 29. A slot 33 is created between the socket 29 and extension 32. The extension and slot is used to fit the mask base 22 to the headgear 21. In this embodiment the extension 32 is substantially curved to follow the shaped of the projection 29. However, in other forms the extension may be substantially straight or otherwise shaped.

In use, the nasal mask is assembled with headgear 21. The headgear 21 in the preferred form is comprised of headgear straps 35, 36, 37, 38 and a substantially curved and elongate member 34. The member 34 is curved and substantially rigid, or at least more rigid than the headgear straps.

The headgear straps 35, 36, 37, 38 are preferably made from a composite foam layered material, such as Breathoprene™. The headgear 21 preferably includes a first strap 35 and a second strap 36. The first strap 35 extends in use over the forehead or top front area of a patient's head. The second strap 36 extends around the back of the patient's head. The headgear 21 also has side straps 37, 38 that in use extend down the cheeks of a patient and the ends of the straps terminate in the upper lip area of the patient in use.

Referring to FIG. 2, the curved and elongate member 34 is comprised of a central section 42 and contoured side arms 41, 54. A substantial length of each of the side arms 41, 54 overlaps and is attached to the side straps 37, 38. However, the side straps 37, 38 only extend partially along the length of the side arms 41, 54 so as to terminate beneath the cheek or near the upper lip region. As the side straps 37, 38 are made from a soil foam type material they provide a comfortable fitting of the headgear and curved member 34, while the substantially rigid side arms 41, 54 provide rigidity and stability to the headgear 21 and nasal mask 2. The attachment between the side straps and rigid extension side arms may be made by gluing, sewing or other appropriate fastening.

Preferably the side arms of the curved member 34 are integrally moulded with the central section 42. The curved member 34 is preferably three dimensionally moulded to a shape to substantially match the cheek contours of a human. The side arms 41, 54 are preferably of thinner width (cross-section) than the central section 42. As the side arms 41, 54 are moulded of a plastics material to be substantially thin they are capable of being bent or adjusted to allow for better and more comfortable fit to a patient. The side arms 41, 54 may also include weakened or narrow areas 39 to allow for additional bending, moulding or twisting of the arms 41, 54 to better fit the headgear to individual patients. For example, in the embodiment shown in FIGS. 2 and 3, the narrowed area 39 corresponds to the cheek bone area of a patient and allows for the side arms 41, 54 to easier bend or twist to fit the contours of the patient's face.

In alternative embodiments the side arms may have weakened areas that are narrower in cross-section to that of the remainder of the side arms. A narrower cross-section area would also provide a weakened area that may be easily manipulated.

In alternative embodiments of the present invention the side straps of the headgear may not extend under and along the length of the curved member but be attached to the distal ends of the straps. This attachment may be by hook and loop material, as is known in the art, or by other attachment methods as known in the art. In this form, the arms of the curved member may have padding underneath them or no padding at all.

Referring to FIG. 3, the curved elongate member has a central section 42 that in an assembled form supports the mask base and body such that the pillows 24, 25 rest against the patient's nares. The central section 42 is a half circle that is integrally moulded with the side arms 41, 54. The central section 42 has a raised area 43 on its exterior, at the apex of the half circle. The raised area 43 is shaped to receive the mask base 22. To assemble, a patient merely needs to slide the mask base 22 into the central section 42 such that the raised area 43 fits into the slot 33 on the mask base 22.

The side arms 41, 54 of the curved member 34 preferably have varying cross-sectional thickness. The ends of the arms 41, 54 attached to the central section 42 are thicker over the most curved parts 55, 56 of the arms, whereas the straighter parts of the arms 57, 58 have a narrow cross-section. Therefore, the thicker ends 55, 56 hold their shape better.

In alternative embodiments, the mask base 22 may be formed integrally with the curved member 34. Therefore, the central section and base would be one and would not be able to be separated from one another.

Figure 20:
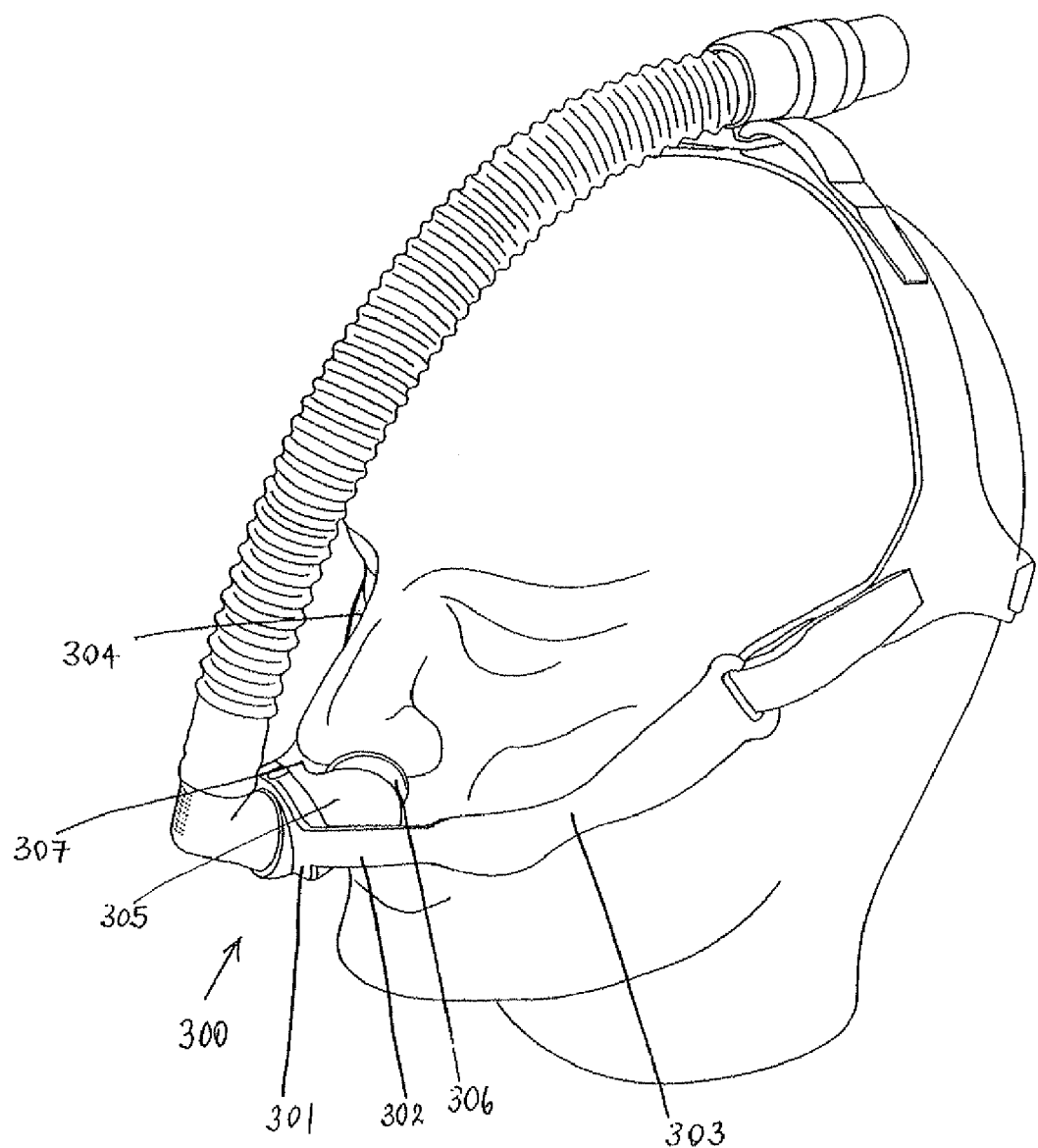
FIG. 20 is a perspective view of an eighth form of a patient interface and headgear of the present invention.
Figure 21:
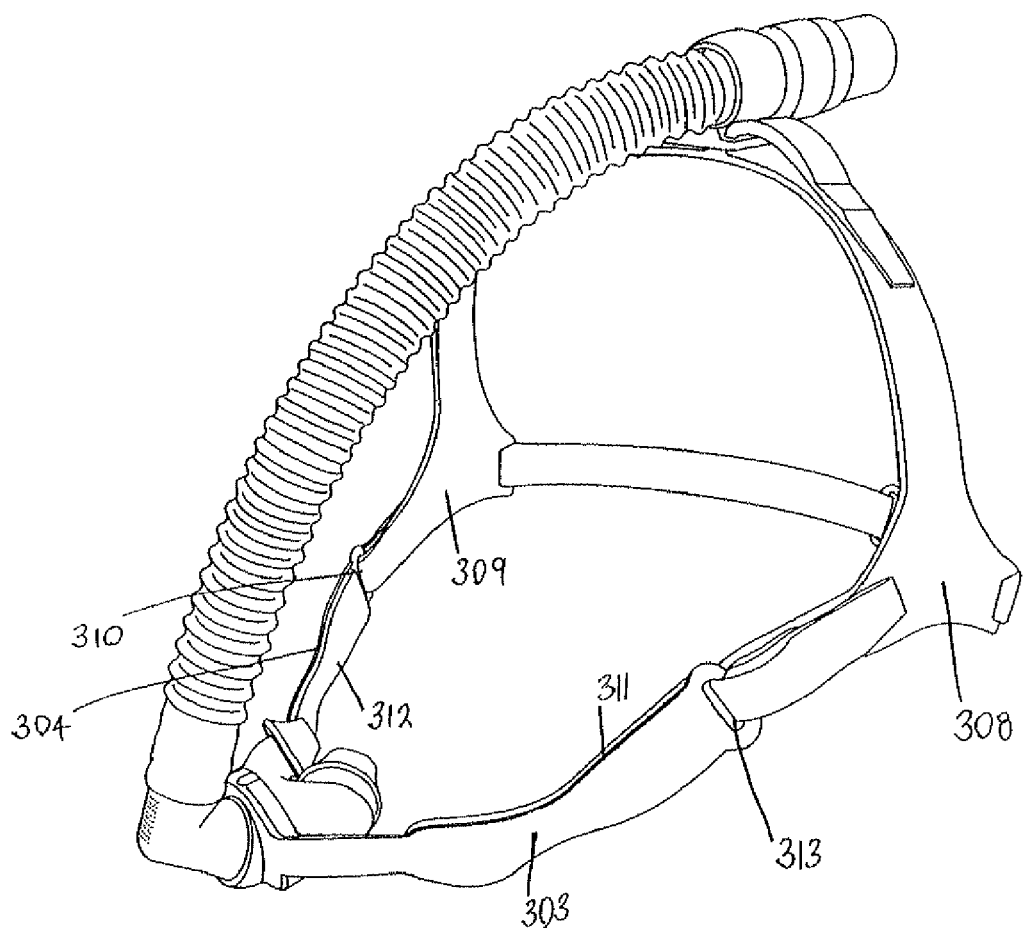
FIG. 21 is a perspective view of the interface and headgear of FIG. 20 showing inner pads on the arms of the headgear.
Figure 22:
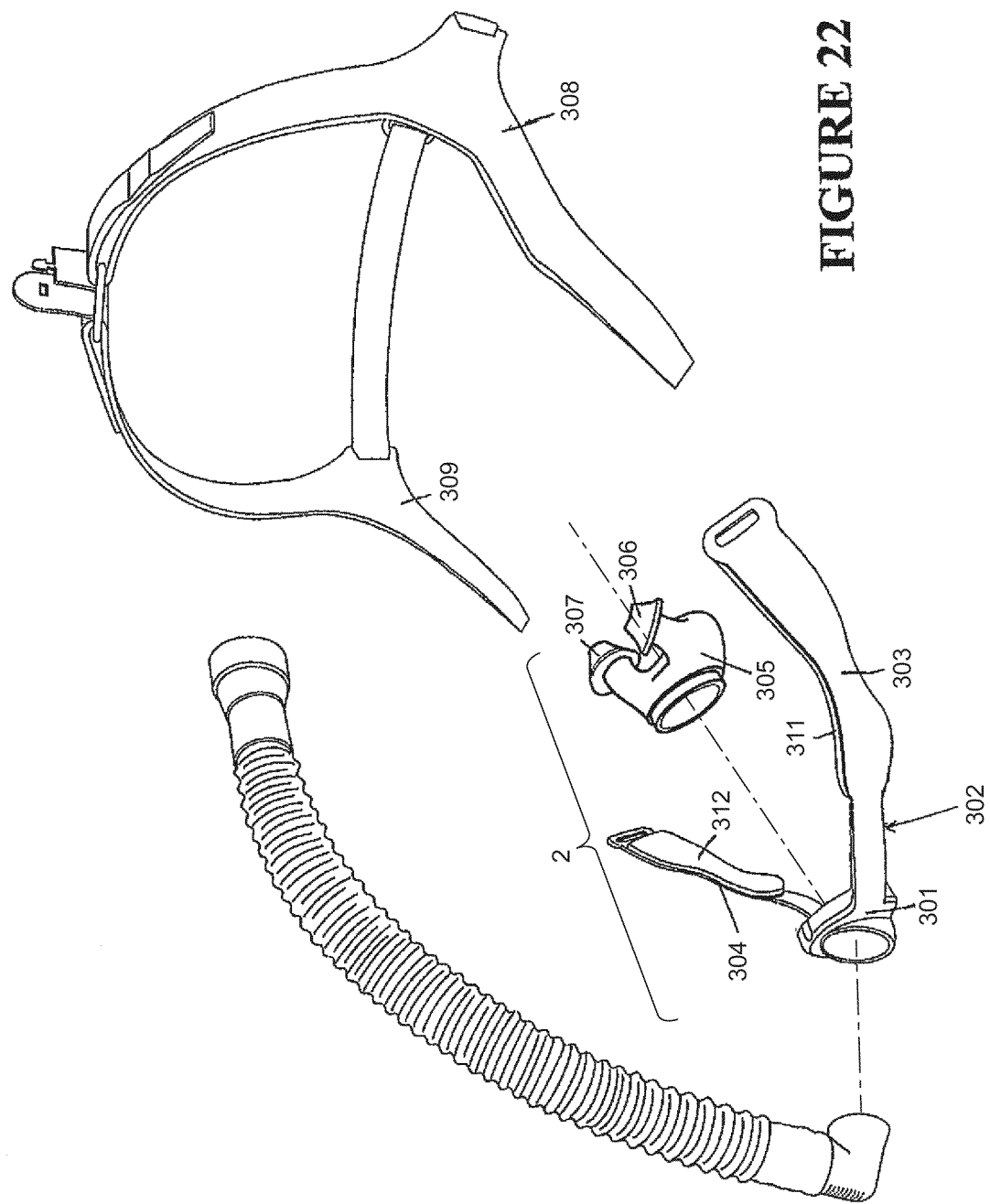
FIG. 22 is an exploded view of the interface and headgear of FIG. 20.

An example of this is shown in FIGS. 20 to 22, the eighth embodiment of the patient interface and headgear 300. Here, the mask base 301 and the curved elongate member 302 are integrally formed, for example, by moulding or the like. The elongate member comprises arms 303, 304 similar to that described above. Also the mask body 305 has integral nasal pillows 306, 307 similar to that described above in relation to FIG. 2.

As can be seen in FIGS. 21 and 22 in this eighth embodiment the headgear straps 308, 309 do not extend down the arms 303, 304 as with other embodiments. In this embodiment the headgear straps 308, 309 attach through recesses 310, 313 at the end of the arms 303, 304 extending along the arms are inner pads 311, 312 that rest against the patient's cheekbones in use and provide comfort to the patient's face. The pads 311, 312 only extend up to near the attachment recesses 309, 310. The pads are preferably made from a foam type material, such as the laminated material that the headgear straps are made from. The pads 311, 312 preferably do not extend beyond the edges of the arms 303, 304.

Referring back to FIGS. 2 and 3, alternatively, the curved member 34 may be formed as two separate pieces. That is, the central section 42 may be formed as two parts with a central split seam, the two left and right halves joined in use. The two left and right parts could either be joined along a seam as described above, with the base 22 slotting into the slot 33 as described above, or alternatively, each of the two left and right arms may be attached one to each side of the base 22.

Where a "substantially continuous elongate member" or "curved member" is referred to in this specification, it refers to any of the options for the curved member 34 outlined above.

The side arms 41, 54 may also include a loop 40 or detached section. This is where a section of the side arms 41 is not attached to the strap 38, 37 lying underneath. Thus the detached section 40 of the side arms forms a loop to which a tubing attachment 44 (such as that shown attached to another strap in FIGS. 2 and 3) may be looped to the side arms 41, 54 and the tubing 31 attached to either of the side arms.

The connector 30 in the preferred form is a ball and socket jointed connector to allow for the tubing 31 to swivel in the mask base 22. The tubing 31 may be attached to any of the headgear straps. However, a tube attachment 44 is shown where the tubing is attached by fasteners, such as hook and loop fastener, to the first strap 35. In other embodiments the tubing 31 may be attached to either the side straps 37, 38 or merely allowed to fall freely from the nasal mask 2.

Although a ball and socket joint, as described above, between the mask base 22 and tubing 31 is preferred other connections may be utilised, such as a flexible piece of silicone, or other appropriate connection. The connection between the base and tubing must be able to be flexed or rotated to allow for the tubing to be moved without causing the dislodgement of the nasal mask 2 from the user's nares.

The mask body 23 may be provided with nasal pillows of various different sizes, such that user's may remove an existing mask body and simply attach a different sized body to the mask base 22.

Figure 8:
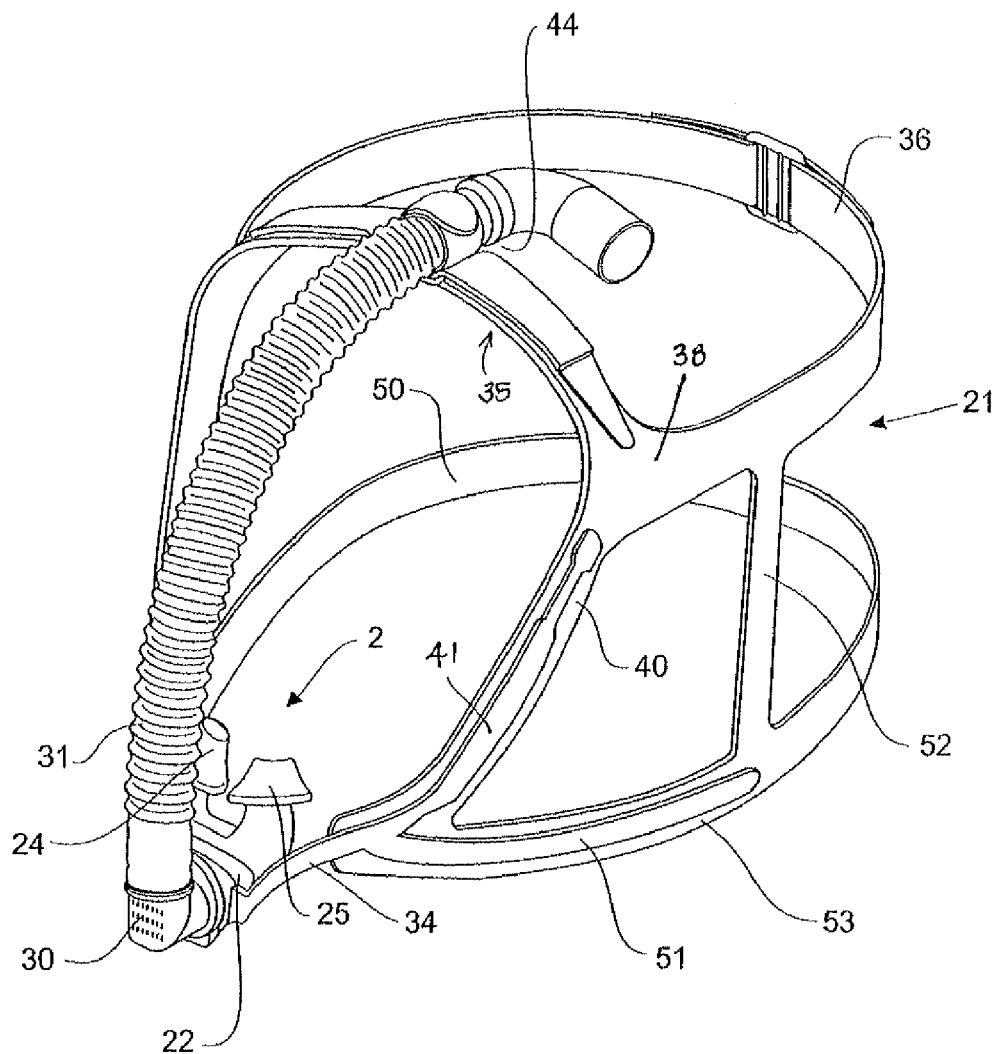
FIG. 8 is a perspective view of a nasal mask of the first form of the present invention but having alternative headgear that includes additional rigid extensions.

Alternative headgear may be used with the patient interface of the present invention. In particular, alternative headgear is shown in use with the first form of the patient interface (of FIG. 2) in FIG. 8. Here the headgear may include an additional strap 53 extending from the cheek region of the side straps 41 and extending behind the user's head. This lower additional strap 53 may also include substantially rigid arms 51 similar to the arms 41 described above. Any number of connecting straps 52 may also be provided between the upper strap 36 and lower strap 53. Again, the arms 51 would provide stability and rigidity to the additional strap 53.

In the embodiment described above, when the patient interface of the first form is in use, the user's face causes the mask base 22 and body 23 to clip with the curved member 34. This is due to the angle of the curved member 34 and fixing of the mask base 22 and body 23 to the curved member 34.

Further, in all forms, the curved member 34 transfers the load of the patient interface away from the user's nose and to the cheek regions of the user.

Figure 9:
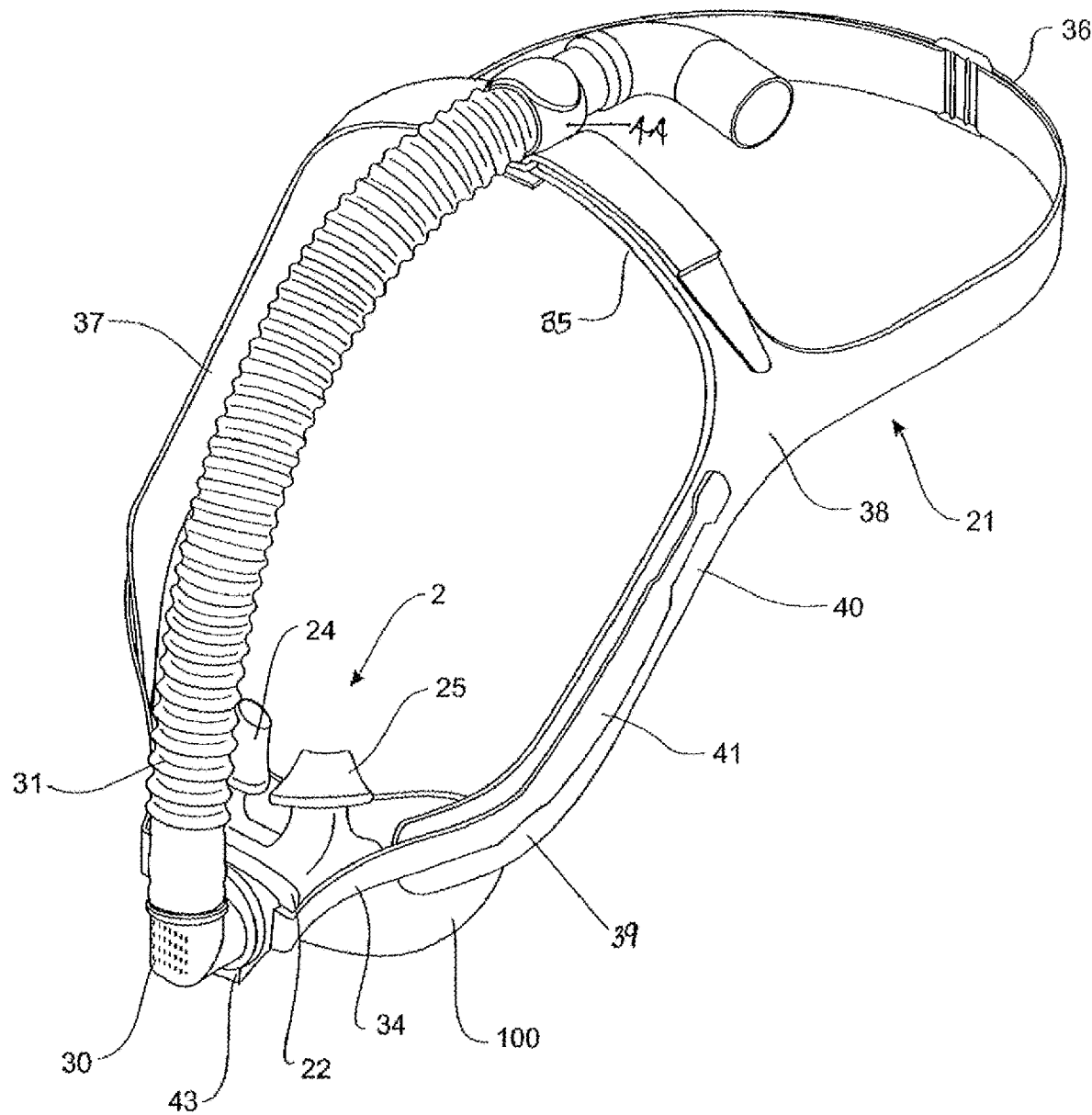
FIG. 9 is perspective view of a second form of a patient interface and headgear of the present invention.
Figure 10:
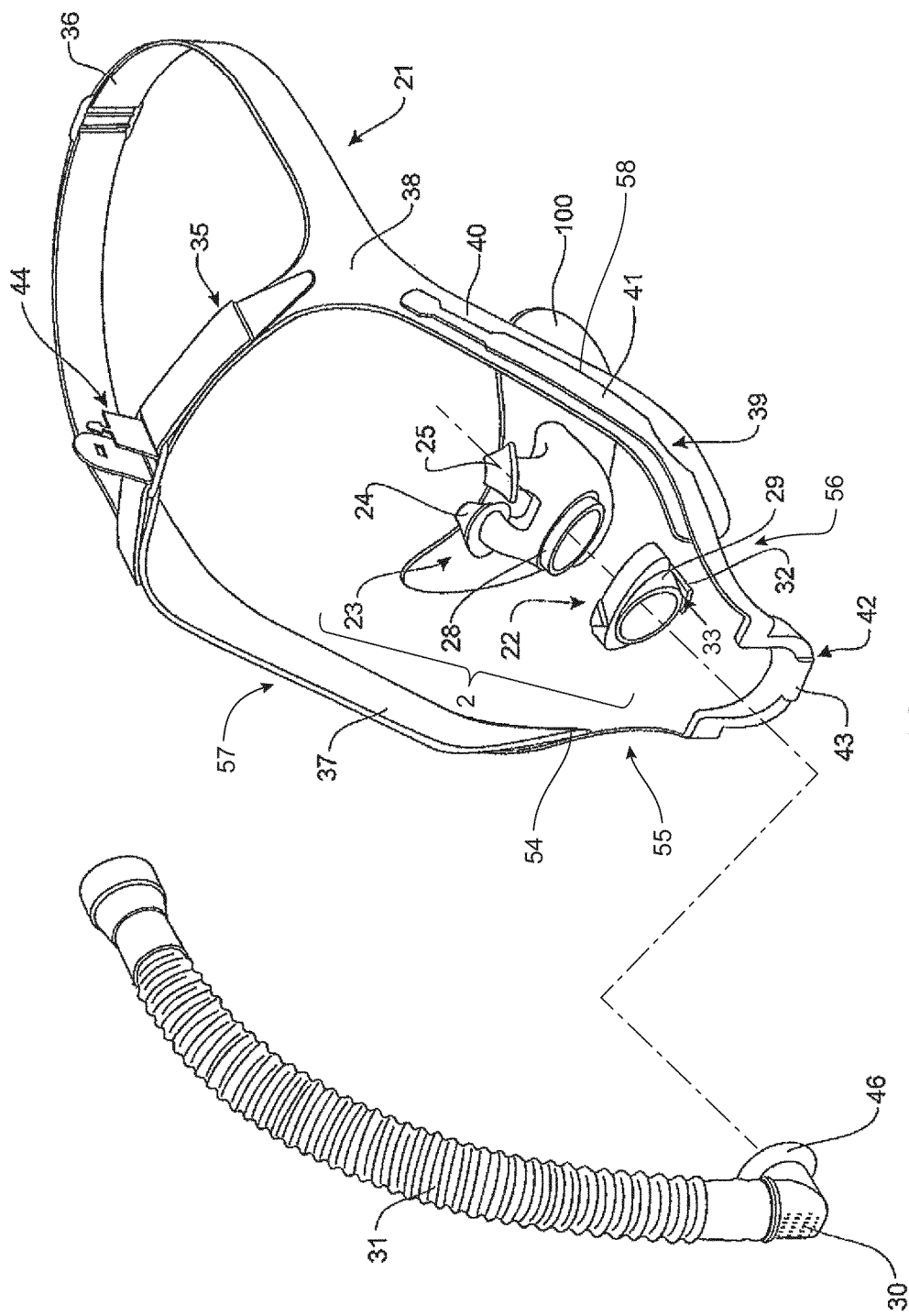
FIG. 10 is an exploded view of the patient interface and headgear of FIG. 9.

A second form of the patient interface and headgear of the present invention is shown in FIGS. 9 and 10. In this embodiment a mouthpiece 100 is attached to the substantially tubular mask body 23 substantially below the nasal pillows 24, 25. The mouthpiece 100 is preferably a flap that is fittable within the patient's mouth. A gases pathway extends through the mask body 23 and through the centre of the mouthpiece 100, such that in use a patient or user is supplied with gases via the nasal pillows 24, 25 and the mouthpiece 100. The flap 100 is preferably made from a silicone plastics material but other appropriate materials such as rubber, thermoset elastomer or thermoplastic elastomer, such as Kraton™ may be used. The flap 100 is preferably integrally moulded with the mask body 23 and nasal pillows 24, 25. In use the flap 100 sits within the user's mouth between the user's teeth and lips.

In this second form the headgear and particularly the curved member 34 is substantially the same as that described in relation to the first embodiment.

Figure 11:
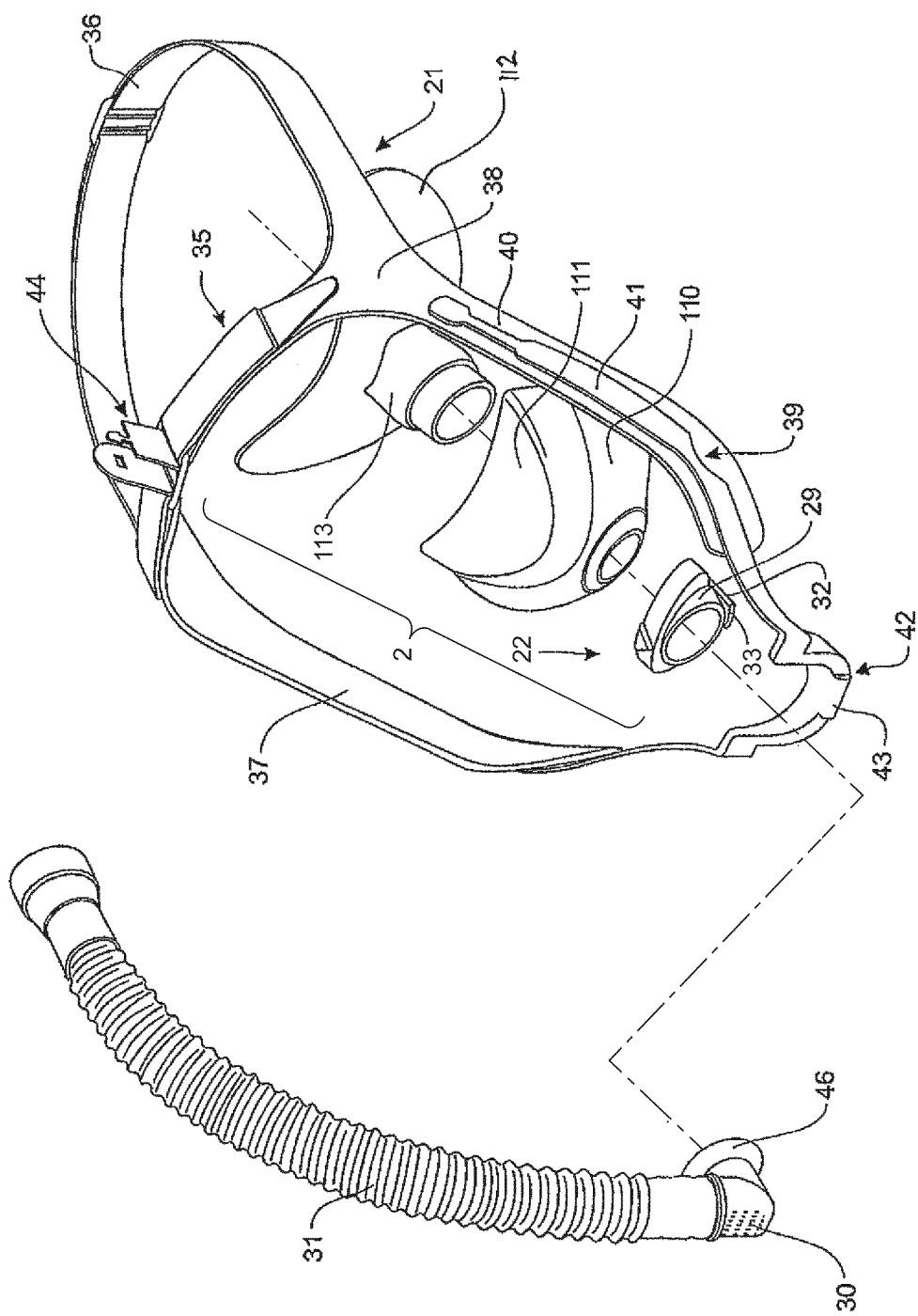
FIG. 11 is an exploded view of a third form of a patient interface and headgear of the present invention.

A third form of the patient interface and headgear of the present invention is shown in FIG. 11. In this embodiment a mouthpiece as well as a nose blocking device is attachable to the mask base 22. The mouthpiece 110 and nose blocking device 111 are preferably integrally formed. The mouthpiece 110 has an inner vestibular shield 112 that is similar to the flap 100 described above. Therefore the vestibular shield 112 in use sits within the patient's mouth between the patient's teeth and lips and provides an at least partial seal between the user and the shield 112.

A tubular extension 113 extends through the mouthpiece 110 to the mask base 22 from the vestibular shield 112. The extension allows for gases to be passed to the patient from the conduit 31.

The nose blocking device 111 in use rests under the user's nose and blocks the user's nares.

In this third form the headgear and particularly the curved member 34 is substantially the same as that described in relation to the first embodiment.

Figure 12:
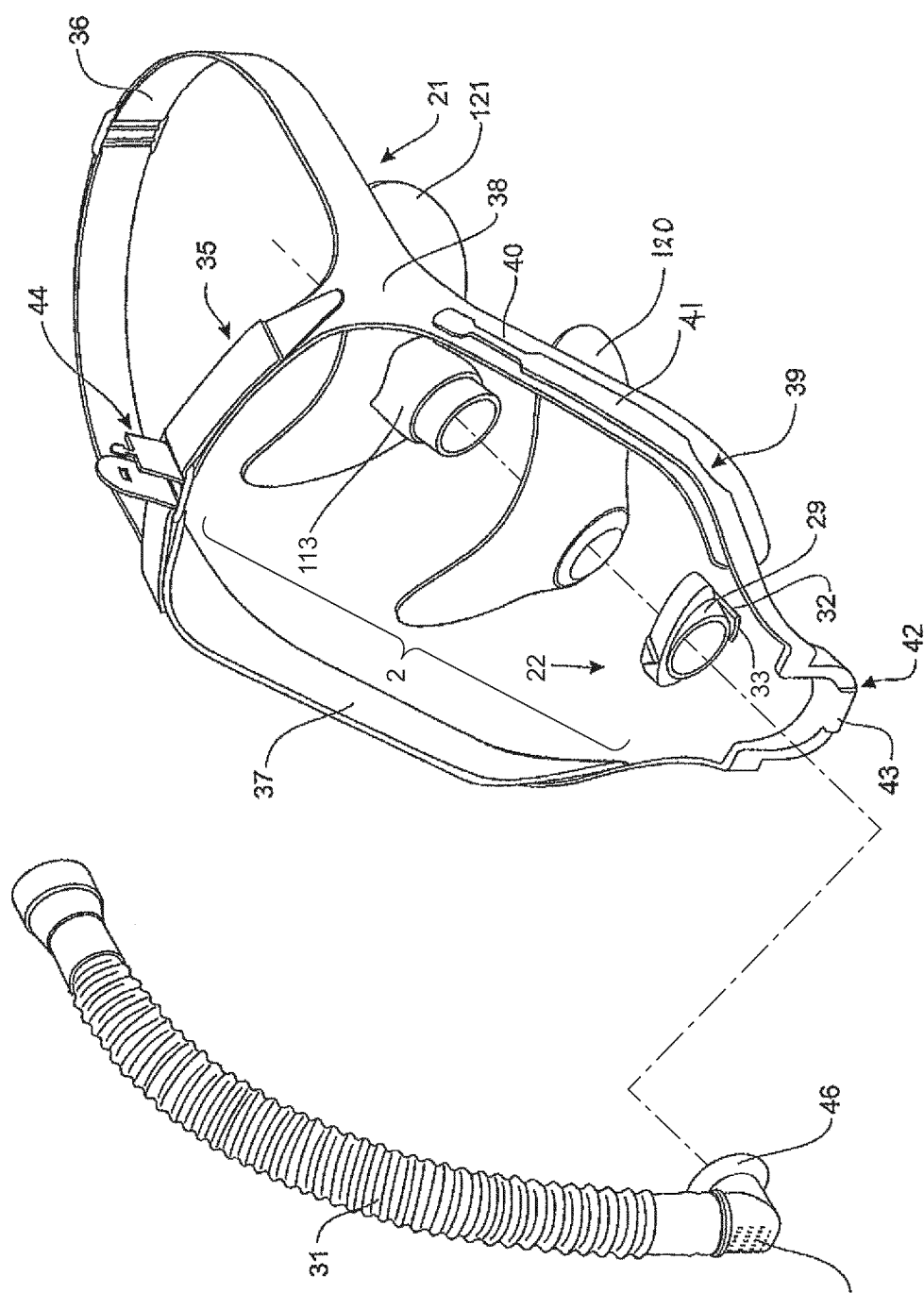
FIG. 12 is an exploded view of a fourth form of a patient interface and headgear of the present invention.

A fourth embodiment of the patient interface and headgear of the present invention is shown in FIG. 12. In this embodiment a mouthpiece 120, 121 is attachable via a tubular extension 122 to the mask base 22. The mouthpiece is made up of an outer mouthpiece flap 120 and an inner vestibular shield 121. The shield 121 is substantially the same as that described in reference to the third embodiment. The outer mouthpiece flap 120 rests in use outside the user's mouth and substantially seals about the user's mouth. The outer mouthpiece flap 120 and an inner vestibular shield 121 are described in further detail in U.S. Pat. No. 6,679,257, the entire contents of which is herein incorporated by reference.

In the fourth form of the headgear and particularly the curved member 34 is substantially the same as that described in relation to the first embodiment.

Figure 13:
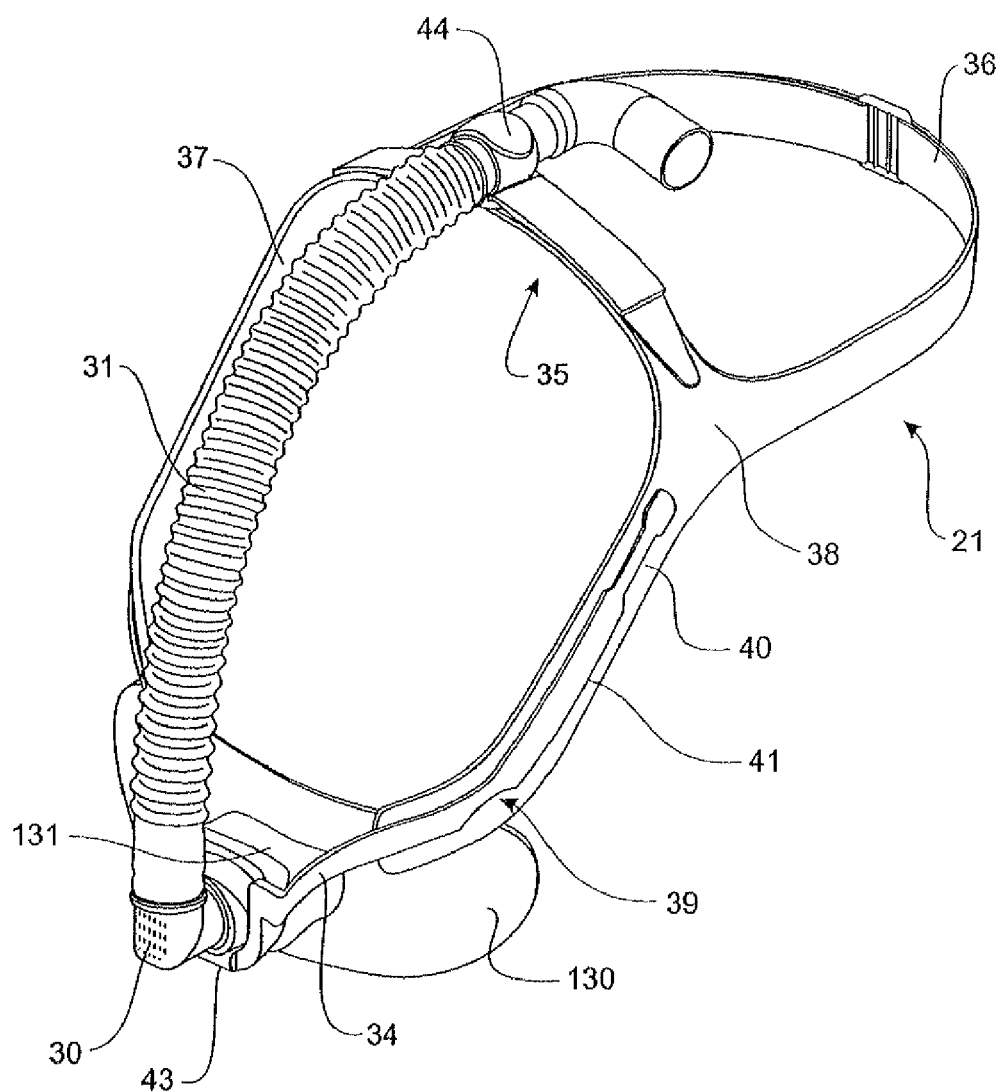
FIG. 13 is a perspective view of a fifth form of a patient interface and headgear of the present invention.
Figure 14:
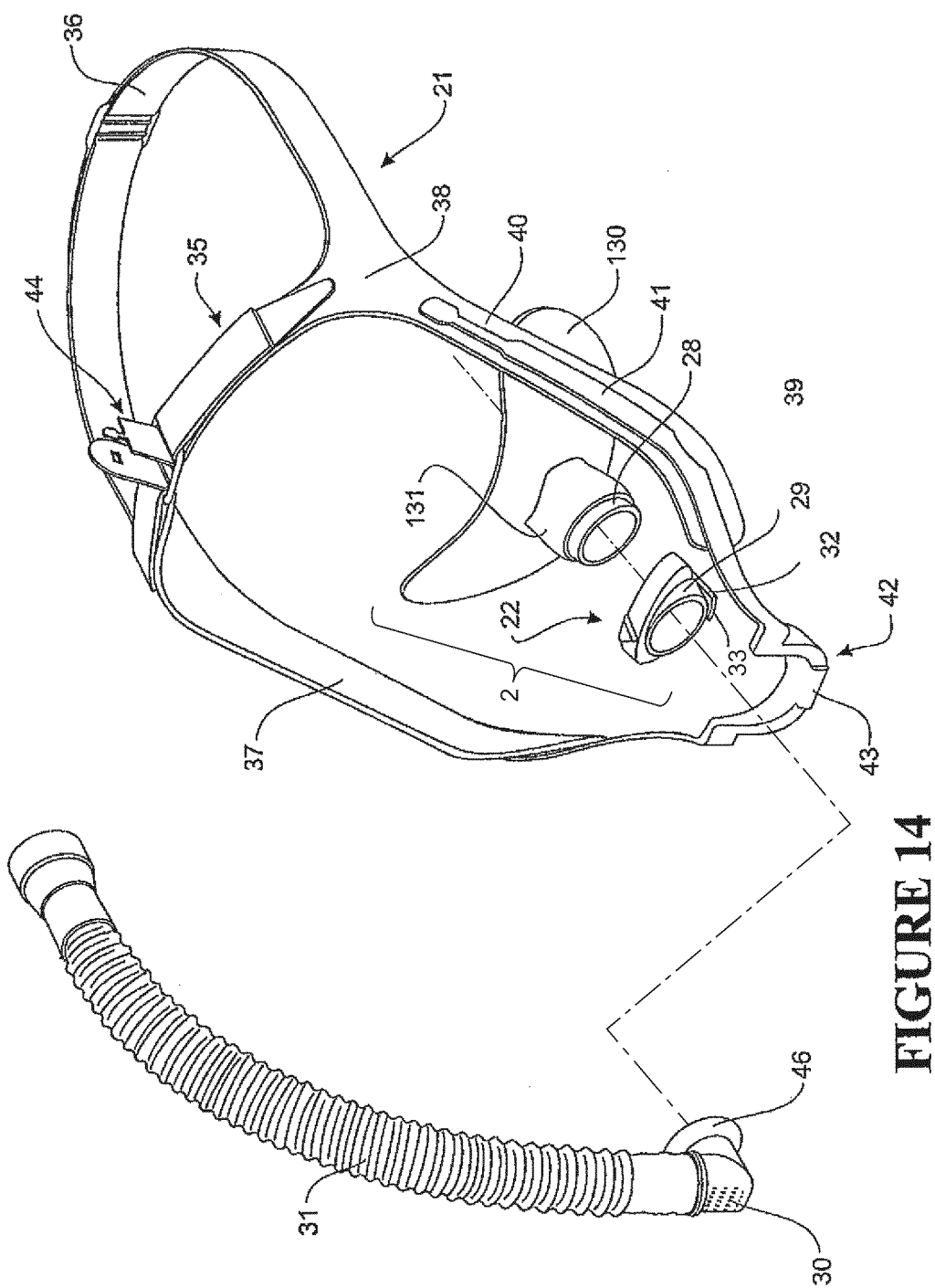
FIG. 14 is an exploded view of the patient interface and headgear of FIG. 13.

A fifth form of the patient interface and headgear of the present invention is shown in FIGS. 13 and 14. This embodiment is very similar to the fourth embodiment except the mouthpiece is simply an outer mouthpiece flap 130. This flap 130 is liftable to the mask base 22 by way of the tubular extension 131. Again, as above, the headgear and particularly the curved member 34 are substantially the same as that described in relation to the first embodiment.

Figure 15:
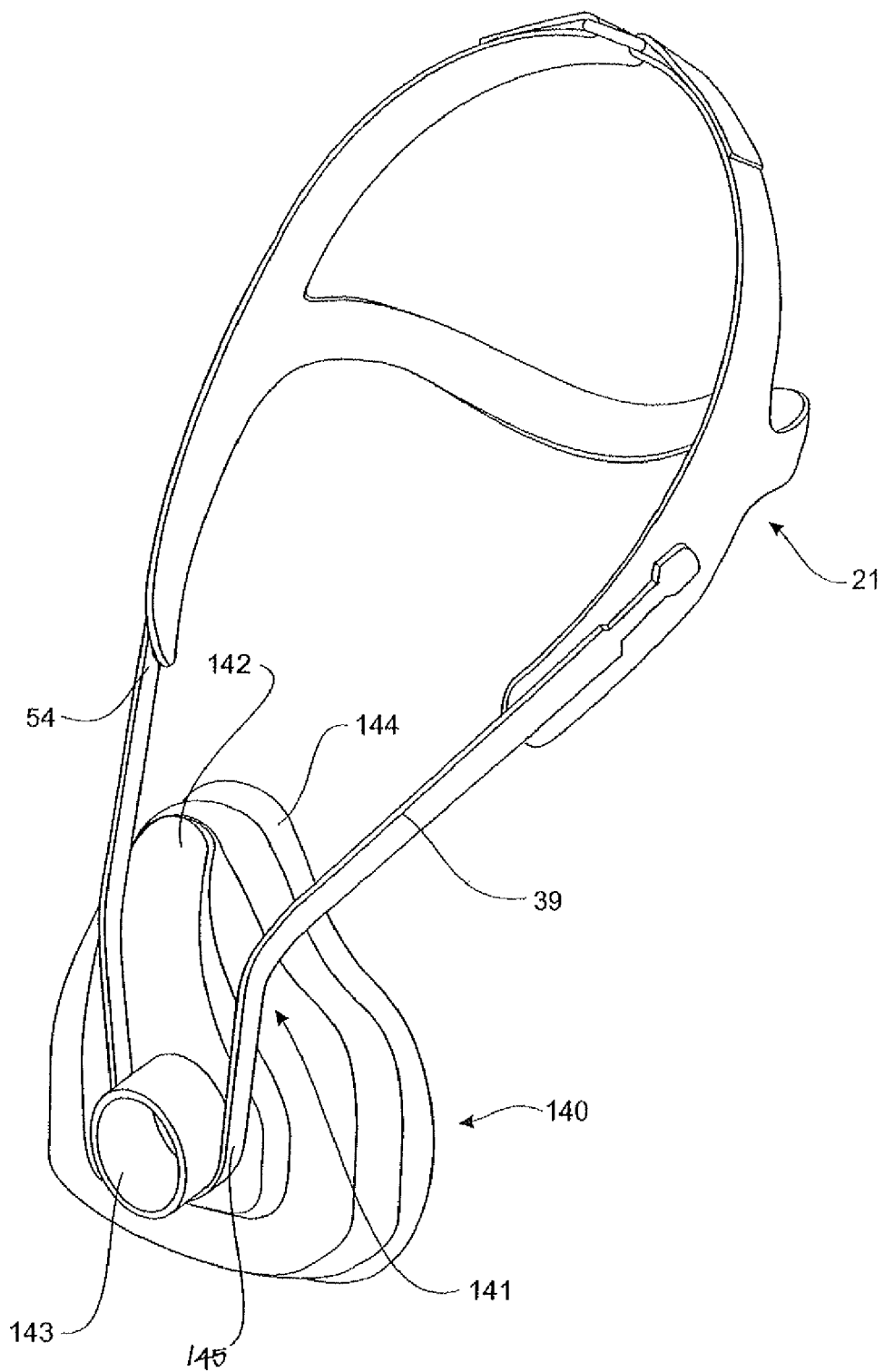
FIG. 15 is a perspective view of a sixth form of a patient interface and headgear of the present invention.

A sixth form of the patient interface and headgear of the present invention is shown in FIG. 15. In this embodiment the patient interface is a full face mask 140 that extends over a user's nose and mouth and under the user's chin in use. The mask 140 has a body 142 made from a substantially rigid plastics material and a cushion 144 made from a substantially soft plastics material. The mask and cushion are preferably similar to that described in more detail in U.S. patent application Ser. No. 11/368,004, the entire contents of which is incorporated herein by reference.

A tubular inlet port 143 is formed in the mask body 142. The tubing 31 is attachable to the port 143 to provide gases to the user wearing the mask.

The headgear is substantially similar to that described in relation to FIG. 2 (the second form); however, the curved member 141 differs. The curved member 141 does not have a mask base similar to that described in the second form in which to attach to. Therefore, the curved member 141 has a central section 145 that curves under the inlet port 143, effectively anchoring on the inlet port. The curved member 141 is moulded in substantially the same manner as described with reference to the second form.

Figure 16:
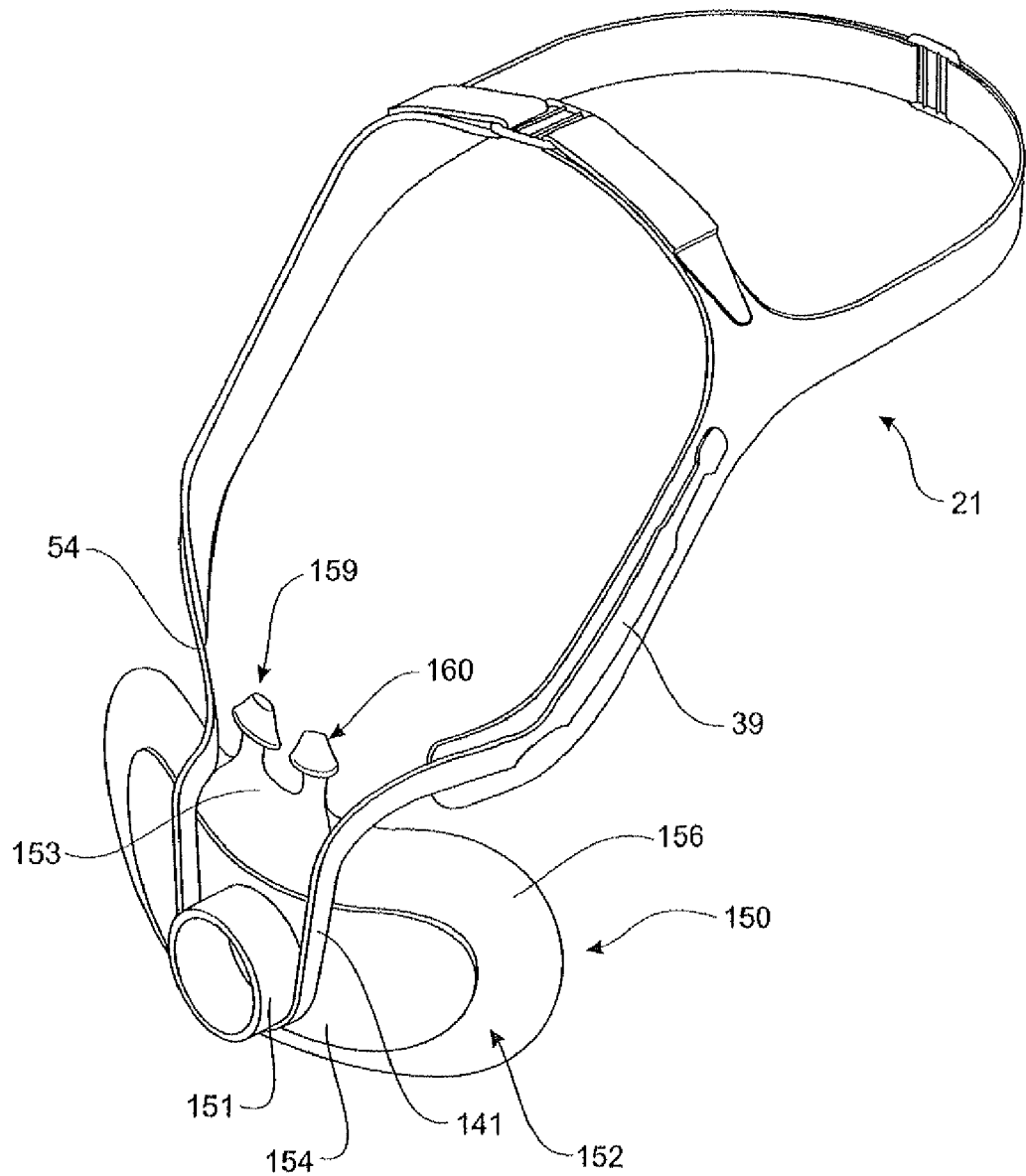
FIG. 16 is a perspective view of a seventh form of a patient interface and headgear of the present invention.
Figure 17:
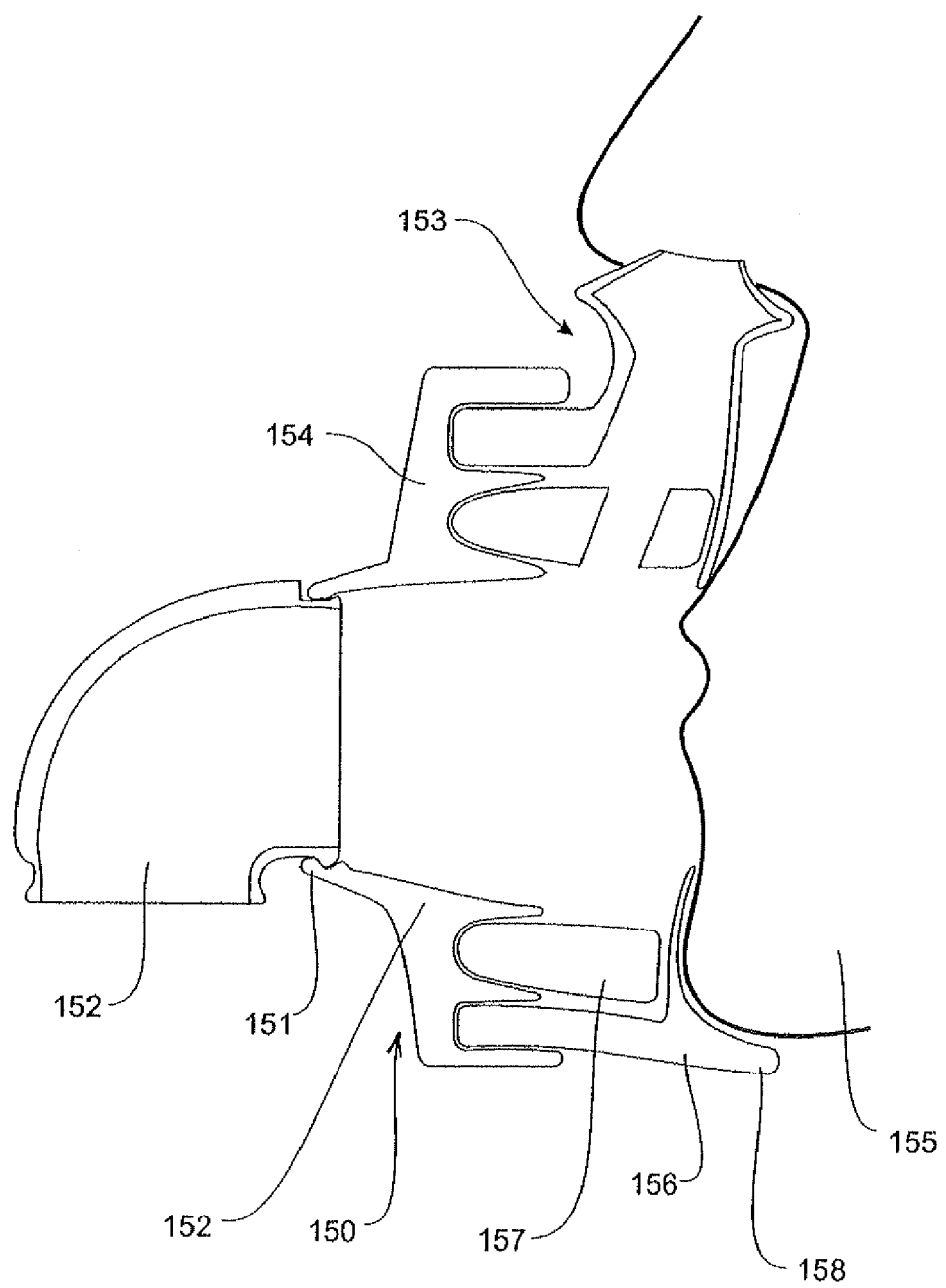
FIG. 17 is a cross-sectional view of the patient interface of FIG. 16.

A seventh form of the patient interface and headgear of the present invention is shown in FIGS. 16 and 17. Here, the headgear and curved member is similar to that described above in the sixth embodiment, where the curved member 141 has a central section that curves under and anchors onto an inlet port 151 on a patient interface 150. The patient interface 150 is an integral mouth mask 152 and nasal pillows 153. The mouth mask 152 preferably extends under the user's 155 chin, as shown in FIG. 17.

The interface 150 has a substantially rigid body 154 that has substantially soft cushion 156 attached to it. The cushion 156 is preferably of the type disclosed in U.S. Pat. No. 6,951,218 (the entire contents of which is incorporated herein by reference) having an inner 157 and outer 158 cushions.

Integrally formed in the outer cushion 158 are nasal pillows 153. Preferably two nasal pillows 159, 160 are formed in the cushion 158. These are substantially tubular and carry gases in use from the inside of the interface 150 to the user's 155 flares. The outer cushion 158 and nasal pillows 159, 160 are preferably made from a soft pliable plastics material such as silicone but other appropriate materials such as rubber or KRATON™ may be used.

Figure 23:
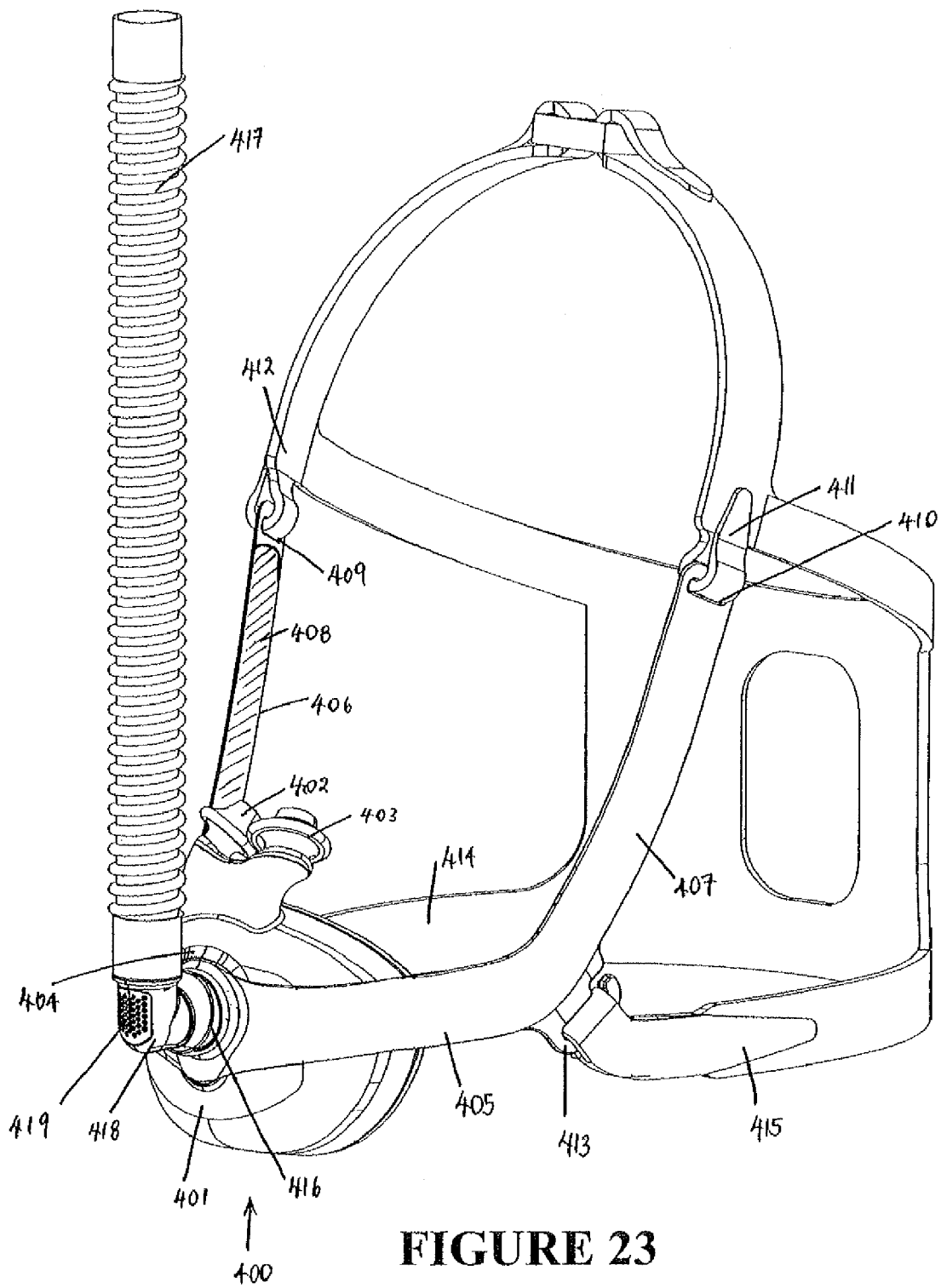
FIG. 23 is a perspective view of a ninth form of a patient interface and headgear the present invention.

A similar but slightly different embodiment to that of FIG. 16 is a ninth embodiment of the present invention, as shown in FIG. 23. Here the interface 400 is substantially the same as the interface 150 of FIGS. 16 and 17. The interface 400 has a body 401 with integral nasal pillows 402, 403. The nasal pillows may be integrally formed with the body or separately formed and simply assembled to the body before use. The nasal pillows 402, 403, as above, are substantially tubular and carry gases in use from the inside of the interface 400 to the user's mires. Again, nasal pillows are preferably made from a soft pliable plastics material such as silicone but other appropriate materials such as rubber or KRATON™ may be used.

In this embodiment the body 401 may be made of a more rigid material than the nasal pillows or simply be made from a soft pliable plastics material as are the nasal pillows.

Attached to an inlet 404 of the body 401 is an elongate member 405 similar to that described in any of the embodiments detailed above, but particularly that of FIGS. 20 to 22. The elongate member 405 has arms 406, 407 that extend along a user's cheekbones then up towards the user's ears when in use. The arms 406, 407 are preferably made from a substantially rigid material, preferably a plastics material. For the users comfort each of the arms 406, 407 have inner pads (only one pad 408 is shown in FIG. 23) extending along their inner sides, particularly where the arms are incident on the user's face.

The arms 406, 407 have recesses 409, 410 at the ends to which headgear straps 411, 412 are attached. The arms 406, 407 may also each have optional side hooks (of which only one side hook 413 is shown), again made out of a substantially rigid material, to which additional side headgear straps 414, 415 may be attached.

At the centre of the elongate member 405 is formed an integral inlet 416 that matches and attaches to the inlet 404 on the body. This integral inlet 416 receives a conduit or tube 417 that is connected in use to a supply of gases. Preferably the tube 417 has a swivelable elbow 418 (for example, a ball joint socket similar to the one described above). Preferably on the elbow 418 are a number of holes 419 that provide an exhaust vent for gases exhaled by the patient in use.

In this ninth embodiment of the patient interface and headgear the interface is a mouth mask and nasal pillows. In alternative forms the patient interface may be a full face mask that is attached to an elongate member and headgear similar in form to those described above and particularly in relation to FIG. 23.

What is claimed is:

1. A mask assembly comprising:
   a cushion comprising a user contacting portion surrounding at least one aperture, the user contacting portion being adapted to rest in sealed manner about a respiratory orifice of a user, in use;
   an elbow connector comprising a proximal elbow portion extending along a first direction and a distal elbow portion extending along a second direction, the second direction extending at an angle relative to the first direction, the elbow connector further comprising an elbow connector inlet configured to be connected to an inspiratory tube and an elbow connector outlet configured to be fluidically connected to the cushion, wherein the elbow connector is configured to allow the elbow connector inlet to swivel relative to the cushion;
   a headgear strap comprising a first end portion, a second end portion, and a central portion, the headgear strap being flexible and formed of a composite foam layered material; and
   a headgear connector member supporting the cushion against the user in use, the headgear connector member comprising a central section integrally formed with a first headgear extension and a second headgear extension as one inseparable member, the first and second headgear extensions being configured to be connectable to the headgear strap and being less flexible than the headgear strap;
   the first headgear extension configured to extend over a left cheek of the user, in use, the first headgear extension having a first distal portion, a first weakened portion integrally moulded with the first distal portion, and a first proximal portion positioned proximally from the first weakened portion, the first distal portion comprising a first distal cross section, the first proximal portion comprising a first proximal cross section, and the first weakened portion comprising a first narrowed cross section smaller than the first distal cross section and the first proximal cross section, such that the first headgear extension is bendable to allow for a more comfortable fit for the user;
   the second headgear extension configured to extend over a right cheek of the user, in use, the second headgear extension having a second distal portion, a second weakened portion integrally moulded with the second distal portion, and a second proximal portion positioned proximally from the second weakened portion, the second distal portion comprising a second distal cross section, the second proximal portion comprising a second proximal cross section, and the second weakened portion comprising a second narrowed cross section smaller than the second distal cross section and the second proximal cross section, such that the second headgear extension is bendable to allow for a more comfortable fit for the user.

2. The mask assembly according to claim 1, wherein both of the first and second headgear extensions comprise distal curved parts with larger cross-sections and proximal straighter parts with narrower cross-sections, the proximal straighter parts being straighter than the distal curved parts, and the larger cross-sections being larger than the narrower cross-sections, so that the distal curved parts hold their shape better than the proximal straighter parts.

3. The mask assembly according to claim 1, wherein the first and second weakened portions are positioned to be over the user's cheek bone area in use.

4. The mask assembly according to claim 1, wherein the first and second weakened portions comprise first and second cross-sections, respectively, that are smaller than cross-sections of portions of the first and second headgear extensions adjacent to the first and second weakened portions, respectively.

5. The mask assembly according to claim 1, wherein the first and second weakened portions comprise smaller cross sections than remainders of the first and second headgear extensions, respectively.

6. The mask assembly according to claim 1, wherein the first headgear extension comprises a first distal end portion and a first proximal end portion, the first distal portion extending proximally from the first distal end portion along a first direction, a first curved portion extending proximally from the first distal portion, wherein the first proximal portion extends proximally from the first curved portion to the first proximal end portion along a second direction at an upward angle relative to the first direction, in use, the first weakened portion being positioned between the first curved portion and the first proximal end portion.

7. The mask assembly according to claim 1, wherein the first distal cross section comprises a first distal thickness and the first narrowed cross section comprises a first reduced thickness that is smaller than the first distal thickness.

8. The mask assembly according to claim 1, wherein the elbow connector outlet is connected to the central section of the headgear connector member.

9. A mask assembly comprising:
a cushion comprising a respiratory gas inlet and a user contacting portion surrounding at least one aperture, the user contacting portion being adapted to rest in sealed manner about a respiratory orifice of a user, in use;
an elbow connector comprising an elbow connector inlet configured to be connected to an inspiratory tube and an elbow connector outlet configured to be fluidically connected to the respiratory gas inlet of the cushion;
a headgear strap comprising a first portion, a second portion, and a central portion, the headgear strap being flexible; and
a headgear connector member supporting the cushion against the user in use, the headgear connector member comprising a central section, a first headgear extension and a second headgear extension integrally moulded with the central section, the headgear connector member being less flexible than the headgear strap;
the first headgear extension extending from a left side of the central section to a first proximal end portion and configured to extend over a left cheek of a user, in use, the first proximal end portion being configured to be connectable to the first portion of the headgear strap, the first headgear extension comprising a thin material such that the first headgear extension is bendable for a better fit to a user, in use, the first headgear extension further comprising a first weakened portion configured to allow for additional bending of the first headgear extension, in use;
the second headgear extension extending from a right side of the central section to a second proximal end portion and configured to extend over a right cheek of a user, in use, the second proximal end portion being configured to be connectable to the second portion of the headgear strap, the second headgear extension comprising a thin material such that the second headgear extension is bendable for a better fit to a user, in use, the second headgear extension further comprising a second weakened portion configured to allow for additional bending of the second headgear extension, in use.

10. The mask assembly according to claim 9, wherein both of the first and second headgear extensions comprise distal curved parts with larger cross-sections and proximal straighter parts with narrower cross-sections, the proximal straighter parts being straighter than the distal curved parts, and the larger cross-sections being larger than the narrower cross-sections, so that the distal curved parts hold their shape better than the proximal straighter parts.

11. The mask assembly according to claim 9, wherein the first headgear extension comprises a first distal end connected to the central section, the first weakened portion being positioned between the first distal end and the first proximal end portion.

12. The mask assembly according to claim 9, wherein the first weakened portion is integrally moulded with the first headgear extension and spaced from the central section.

13. The mask assembly according to claim 9, wherein the first and second weakened portions comprise first and second cross sections, respectively, that are smaller than cross sections of remainders of the first and second headgear extensions, respectively.

14. The mask assembly according to claim 9, wherein the first and second weakened portions comprise narrower cross-sections than adjacent portions of the first and second headgear extensions that are adjacent to the first and second weakened portions.

15. The mask assembly according to claim 9 additionally comprising a headgear connector inlet, wherein the central section, the first headgear extension and the second headgear extension are formed from a single moulded part extending over at least a portion of the headgear connector inlet.

16. A mask assembly comprising:
a cushion comprising a user contacting portion surrounding at least one aperture, the user contacting portion being adapted to rest in sealed manner about a respiratory orifice of a user, in use;
an elbow connector comprising an elbow connector inlet configured to be connected to an inspiratory tube and an elbow connector outlet configured to be fluidically connected to the cushion, wherein the elbow, connector is configured to allow the elbow connector inlet to swivel relative to the cushion;
a headgear strap comprising a first portion, a second portion, and a central portion disposed between the first and second portions; and
a headgear connector member supporting the cushion against the user in use, the headgear connector member comprising a central section, a first headgear extension and a second headgear extension formed as one inseparable member, the first and second headgear extensions being configured to be connectable to the headgear strap and being less flexible than the headgear strap;
the first headgear extension configured to extend over a left cheek of the user, in use, the first headgear extension having a first distal portion connected to the central section, a first proximal portion configured to be connectable to the first portion of the headgear strap, and a first curved portion positioned between the first distal portion and the first proximal portion at a location spaced away from the central section, the first distal portion extending from the central section along a first direction and the first proximal portion extending along a second direction at an angle relative to the first direction, the first headgear extension further comprising a first weakened portion configured to allow the first weakened portion to be more easily bent, the first distal portion, the first proximal portion, the first curved portion, and the first weakened portion being integrally moulded together;

the second headgear extension configured to extend over a right cheek of the user, in use, the second headgear extension having a second distal portion connected to the central section, a second proximal portion configured to be connectable to the second portion of the headgear strap, and a second curved portion positioned between the second distal portion and second proximal portion, the second distal portion extending from the central section along a third direction and the second proximal portion extending along a fourth direction at an angle relative to the third direction, the second headgear extension further comprising a second weakened portion configured to allow the second weakened portion to be more easily bent the second distal portion, the second proximal portion, the second curved portion, and the second weakened portion being integrally moulded together.

17. The mask assembly according to claim 16, wherein the first and second weakened portions comprise narrower cross sections than remainders of the first and second headgear extensions, respectively.

18. The mask assembly according to claim 16, wherein the first and second weakened portions are disposed at the first and second curved portions, respectively.

19. The mask assembly according to claim 16, wherein the first distal portion comprises a distal thickness, the first proximal portion comprises a proximal thickness, and the first weakened portion comprises a reduced thickness that is smaller than the distal thickness and the proximal thickness.

20. The mask assembly according to claim 1, wherein the central section comprises an uppermost edge and wherein there are no headgear extensions extending from the uppermost edge of the central section.

21. The mask assembly according to claim 1, wherein the central section comprises an uppermost edge, a left lateral side and a right lateral side, the first distal portion extending from the left lateral side of the central section lower than the uppermost edge of the central section and the first proximal portion positioned higher than the uppermost edge of the central section, in use, and wherein the second distal portion extends from the right lateral side of the central section lower than the uppermost edge of the central section, the second proximal portion being positioned higher than the uppermost edge of the central section, in use.

22. The mask assembly according to claim 1, wherein the central section comprises an uppermost edge, a left lateral side and a right lateral side, and all headgear extensions of the headgear connector members extend from either the left or right lateral sides of the central section, below the uppermost edge of the central section.

23. The mask assembly according to claim 9, wherein the central section comprises an uppermost edge and wherein there are no headgear extensions extending from the uppermost edge of the central section.

24. The mask assembly according to claim 9, wherein the central section comprises an uppermost edge, the first proximal end portion being at a position higher than the uppermost edge of the central section, in use, and the second proximal end portion being at a position higher than the uppermost edge of the central section, in use.

25. The mask assembly according to claim 9, wherein the central section comprises a left lateral side and a right lateral side, and all headgear extensions of the headgear connector member extend from either the left or right lateral sides of the central section.

26. The mask assembly according to claim 16, wherein the central section comprises an uppermost edge and wherein there are no headgear extensions extending from the uppermost edge of the central section.

27. The mask assembly according to claim 16, wherein the central section comprises an uppermost edge, a left lateral side and a right lateral side, the first distal portion connected to the left lateral side of the central section, lower than the uppermost edge of the central section, the first proximal portion configured to be at a position higher than the uppermost edge of the central section, in use, and the second distal portion being connected to the right lateral side of the central section, lower than the uppermost edge of the central section, the second proximal portion being configured to be at a position higher than the uppermost edge of the central section, in use.

28. The mask assembly according to claim 16, wherein the central section comprises a left lateral side and a right lateral side, and wherein all headgear extensions of the headgear connector member extend from either left or right lateral sides of the central section.

* * * * *